United States Patent

Resnick et al.

Patent Number: 5,220,022
Date of Patent: * Jun. 15, 1993

[54] COMPOSITIONS USEFUL AS DOT PROMOTING AGENTS

[75] Inventors: Bruce M. Resnick, Binghamton; Allan J. Wexler, Endicott, both of N.Y.

[73] Assignee: International Paper Co., Tuxedo, N.Y.

[*] Notice: The portion of the term of this patent subsequent to Jan. 28, 2008 has been disclaimed.

[21] Appl. No.: 646,676

[22] Filed: Jan. 28, 1991

Related U.S. Application Data

[60] Continuation of Ser. No. 339,882, Apr. 17, 1989, Pat. No. 4,997,980, which is a continuation of Ser. No. 29,857, Mar. 24, 1987, abandoned, which is a division of Ser. No. 780,578, Sep. 26, 1985, Pat. No. 4,686,167.

[51] Int. Cl.$^5$ .................. C07D 265/30; C07C 335/20
[52] U.S. Cl. .................. 544/160; 544/163; 544/168; 548/183; 558/415; 558/417; 560/16; 560/34; 562/426; 562/432; 562/439; 564/27; 564/50; 564/51; 564/74; 564/77; 564/148; 564/149; 564/150
[58] Field of Search .......... 564/27, 50, 51, 148, 564/149, 150, 151; 544/160, 165; 548/183; 562/432; 560/9, 34; 260/404.5

[56] References Cited

U.S. PATENT DOCUMENTS 4,997,980 3/1991 Resnick et al. .................. 564/27

Primary Examiner—Glennon H. Hollrah
Assistant Examiner—Shailendra Kumar
Attorney, Agent, or Firm—Darby & Darby

[57] ABSTRACT

Disclosed are novel compounds of the formula

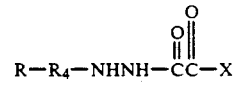

wherein: R is

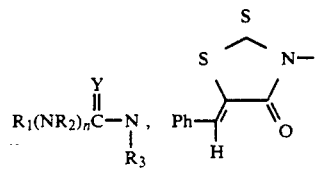

where
Ph is phenyl, or

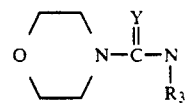

X is $-NR_5R_6$ or $-OR_7$;
$R_1$ and $R_2$ are independently hydrogen, methyl, ethyl, cyclohexyl,

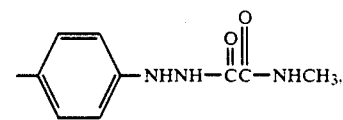

butyl, or heptyl;
$R_4$ is o-phenylene or p-phenylene and $R_4$ can be alkyl- halo- or alkoxy- substituted;
$R_3$ is hydrogen;
$R_5$, $R_6$, and $R_7$ are independently hydrogen, methyl, ethyl, tert-butyl, isobutyl, butyl, alkoxy, acyl, acylamino, aryl, amino, cyclohexyl, aminoalkyl and substituted or unsubstituted phenylamino;
Y is sulfur and oxygen atom; and n is zero or 1; provided n=1 when Y is sulfur.

14 Claims, No Drawings

COMPOSITIONS USEFUL AS DOT PROMOTING AGENTS

This is a continuation of application Ser. No. 339,882, filed Apr. 17, 1989, now U.S. Pat. No. 4,997,980, which is in turn a Rule 62 continuation of Ser. No. 029,857, filed Mar. 24, 1987, now abandoned, which is in turn a Rule 60 division of Ser. No. 780,578, filed Sep. 26, 1985, now U.S. Pat. No. 4,686,167.

BACKGROUND OF THE INVENTION

1. Field of the Invention

One aspect of the present invention relates to a process for forming a photographic image using a silver halide light-sensitive material. More particularly, it relates to a process for forming a high-contrast negative image which simultaneously permits the production of dots possessing high image quality as is necessary in the field of graphic arts. Another aspect of the present invention relates to novel ethanedioic acid hydrazide compounds and compositions containing such compounds, said compounds and compositions being useful as dot-promoting agents in negative-working image systems.

2. Description of the Prior Art

In letterpress and offset lithography, tones cannot be reproduced by varying the amount of ink. A printing press can print only a solid color in the image areas, while leaving the non-image areas free of ink. In order to reproduce pictures in varying tones, graphic-arts photography uses a halftone screen. Halftone photography makes the printing of continuous-tone photographs possible by converting the continuous-tone image into a pattern of small and clearly defined dots ranging in size from 80 to 200 or more dots per inch according to the different amounts of light that are reflected from the different tones of the original.

All halftone dots have a fringe area surrounding them. When a printing plate is made of the halftone with a wide fringe area, the fringe around the dot is also partially exposed. Although it may not be apparent on the plate (i.e., the dot may appear to be of the correct size), once the plate is run on the press, the fringe area may eventually take ink which will fill in the shadow detail. Improvements in dot quality especially in regard to high-edge sharpness and minimal fringe (i.e., a "hard" dot) are therefore extremely important to the printing industry.

Traditionally, the production of high quality dot images was obtained with the use of "lith" films and chemistry. These films, used for making halftone or line images, were capable of producing extremely high contrast and good image sharpness. In the case of halftone images, such properties contribute to high "dot quality", i.e., the production of halftone dots of high density and sharpness. Sharpness is quantified in terms of "edge gradient" which is the ratio of change in density to distance at the boundary between the darkened part and the undarkened part of the photographic image. In general, the higher the edge gradient, the sharper the image (i.e. the "harder" the dot).

Those skilled in the art attribute the formation of hard dots produced with lith materials to the high contrast obtained from infectious development as described by Yule, J. Frank. Inst. 239 221 (1945). In fact, high contrast has come to be synonymous with high edge gradient. However, applicant has observed that a photographic element possessing high contrast is necessary but by no means sufficient to produce a hard dot. In addition, as Hirano (U.S. Pat. No. 4,429,036) states: "for use in the application of plate-making using a contact screen, such images having only the photographic characteristics of high contrast wherein the gradient is 10 or more are inferior in dot quality, are of too high contrast in screen range and therefore are not satisfactory." Thus, the high contrast of the element in and of itself may actually product a screen range which is unacceptably short.

The photographic element must possess a wide screen range which allows good tone reproduction. This is obtained when the darkest area of the subject prints on the press as a solid and the lightest area prints with no evidence of a screen. The films may have very small unprintable dots in these areas which close up in the shadows and disappear in the highlights during printing; however, no loss of intermediate tones due to high contrast is allowable. Conversely, low contrast causes shadows to appear as 80–90% dots and 10–20% in the highlights; this, also, is unacceptable if a faithful reproduction is to be obtained.

Thus, although the dot quality derived from lith materials is excellent, the lith system suffers from serious deficiencies which restrict its utility.

As practitioners of the art recognize, the deficiencies of the lith system include a shortened useful life for the processing chemistry (due to the lack of sulfite) and a lower sensitivity for the lith photographic compositions (because it is necessary to use chloride or chlorobromide emulsions). Other problems inherent in the lith system include pepper spots, drag streaks, narrow screen range, and differences in sensitivity and gradation depending upon the manner in which materials are processed (tray vs. automatic processor).

Mifune (U.S. Pat. No. 4,323,643) discloses an alternative method for producing high quality dot images that solves some of the problems inherent in the lith system. The method involves the use of ureidophenylformyl hydrazide derivatives as additives to negative-working emulsions for the purpose of providing good dot quality. The mechanism by which the preferred agents operate is not mentioned. Mifune presents comparative data showing that various analogs (shown below in Table 1) do not produce acceptable dot quality as is required for the printing industry. Nevertheless, these same agents are reported in the prior art to produce high contrast negative images.

TABLE A

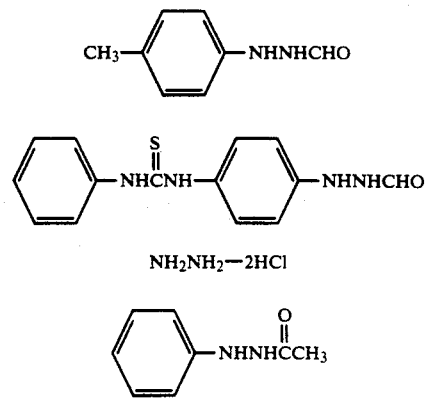

TABLE A-continued

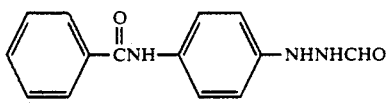

Many examples in the prior art disclose the use of hydrazine derivatives as contrast-promoting agents but the Mifune patent is the only one known to applicant in disclosing a select family of hydrazides that also produce good dot quality.

U.S. Pat. No. 2,419,975 teaches that high-contrast negative photographic characteristics can be obtained by adding a hydrazine compound to a silver halide photographic emulsion. The compounds listed in this patent are hydrazine derivatives that vary considerably in structure, but the quality of the screen dots obtained using these agents is not characterized. In general, large quantities of the disclosed agents are necessary to produce the desired high-contrast effect.

Recent patents teach that the most efficient hydrazines employ a combination of substituents to balance activity and stability. The stability of hydrazines was shown to be further increased by attaching directly to one of the nitrogen atoms a tertiary carbon atom (e.g., a carbon atom located in an aromatic ring). The art has long recognized that the activity of these stabilized hydrazines can be increased by the direct attachment of an acyl group to the remaining nitrogen. Presently, only a few substituents attached to the acyl carbonyl functionality have demonstrated utility in a negative-working, high-contrast system. These substituents include hydrogen (most preferred), unsubstituted alkyl (the activity of which dramatically falls as the chain length is increased) and, less desirably, aryl which is preferrably substituted with electron-donating substituents (electron withdrawing substituents reduce the activity of the phenyl benzoic acid hydrazide). For example, Simson and Jordan (Canadian Patent No. 1,146,001 pp 15 line 16-24) state: "Although the hydrazine compounds intended for use in the practice of this invention each contain a formyl moiety, it is appreciated that otherwise comparable hydrazine compounds containing a benzoyl moiety substituted with a highly electron-withdrawing substituent such as a cyano group are operative. Such compounds have, however, been found to be inferior to the hydrazine compounds containing a formyl group."

Thus, the most commonly employed hydrazines are aryl formyl hydrazides. The more soluble agents of this class can be incorporated into the processing solution, but if they are to be incorporated into the photographic element, their mobility is preferably reduced. This can be achieved by incorporating either a ballast group or a functionality that promotes adsorption to the silver halide grain surface. The selection of an adsorption-promoting substituent for a phenyl hydrazide is limited in that "Tightly adsorbed aryl hydrazides are not usually efficient in increasing the contrast in negative-working silver halide emulsions. It is believed that contrast is increased by infectious development and that undue restriction of mobility interferes with the ability of the aryl hydrazides to promote infectious development" Parton, U.S. Pat. No. 4,459,347. The delicate balance necessary to provide adsorptivity to the silver halide grain while still providing adequate solubility, as well as the requirement for stability and inherent activity, place serious constraints upon the design of new aryl hydrazide contrast-enhancing agents.

When groups such as thiourea, thioamide, heterocyclic rings, or urea are used as adsorption-promoting functionalities, the molar concentration of the hydrazide can be reduced by an order of magnitude without loss of activity. This is a significant advantage over the use of mobile hydrazines because, at the high concentration necessary to exhibit contrast enhancement in a negative emulsion, these mobile hydrazines release sufficient nitrogen to disrupt the ordered array of the photographic element and thereby deteriorate the image quality. Furthermore, diffusion of the mobile hydrazines into the processing chemistry alters the properties of the chemistry with time. Finally, the adsorption-promoting hydrazides are said to be less sensitive to the degree of stirring and temperature variation in the processing chemistry. This is a significant factor in reducing the differences in photographic speed and contrast found between tray and automatic developing for a given photographic emulsion.

Significantly, although both the mobile hydrazides and the adsorption-promoting hydrazides substantially increase the contrast of a photographic emulsion, only a select few of the latter class also improve dot quality. Undoubtedly, the dual constraints on controlled adsorptivity of the hydrazide and the printing parameters, which require tight control on screen range, severely limit the initially large number of choices of hydrazide derivatives that produce high contrast; it follows then that these constraints also limit the number of agents that can produce high quality dots since high contrast is a necessary factor in producing high-quality dots.

Despite the many advantages of photographic elements containing non-diffusable aryl hydrazides of the type found in U.S. Pat. No. 4,323,643, several defects still remain.

One such defect is that elements containing the non-diffusing hydrazides of the prior art have an even narrower screen range than that found in lith systems. This deficiency makes it increasingly difficult to accurately record all the detail in both the shadow and highlight areas of the continuous tone original. In general, the narrower the screen range, the harder (steeper) the dot gradation and hence the higher the contrast. Because the contract of a silver halide emulsion containing an aryl hydrazide is dependent upon the particular aryl hydrazide, it would be most desirable to obtain contrast-enhancing agents producing a wider (softer) screen range.

Aryl hydrazides of the prior art have a tendency to produce dark spots on portions of the image that have not been (or have been only partially) exposed. These spots are known as "pepper grain". This phenomenon is observed as the concentration of the aryl hydrazide is increased and its onset generally coincides with the concentration necessary to produce contrast enhancement. As the processing chemistry becomes oxidized, on prolonged exposure to the air, pepper grain becomes more frequent and more pronounced.

A third and perhaps most serious defect associated with the use of the nondiffusing hydrazides of the prior art is their dependence on processing chemistry temperature. Attempts to solve this problem have included combining a nondiffusing hydrazide having a positive temperature dependency with other hydrazine derivatives that have a negative temperature dependency. U.S. Pat. No. 4,416,969 teaches the use of benzotriazole phenyl hydrazides in combination with thiourea-substituted phenyl hydrazides for the purpose of improving this temperature dependency.

In regard to the prior art relating to the present invention, Trivelli (U.S. Pat. No. 2,419,975) discusses the use of oxalyl hydrazide as a contrast-and speed-enhancing agent in a negative-working emulsion whereas Whitmore (U.S. Pat. No. 3,227,552) discusses the use of ethoxalyl-2-phenyl hydrazide in a direct-positive emulsion. Neither patent discloses the use of these agents for the production of high edge-quality dots. Considering Mifune's results with the thioureidophenyl formyl hydrazide, there would be no reason for those skilled in the art to expect that oxyalyl hydrazides substituted with adsorption-promoting functionalities (such as thioureido) would afford any benefit or advantage in producing high edge quality dots.

It has now been unexpectedly discovered that oxalyl hydrazides substituted with a variety of substituents (e.g., thioureas, ureas, amides and heterocycles) attached to the phenyl ring impart excellent dot quality properties. Moreover, unlike the ureidophenyl formyl hydrazide series that apparently allows substitution on all sites of the phenyl ring, the compounds of the present invention require that the adsorption-promoting group be attached on the phenyl ring either ortho-or para- relative to the oxalyl hydrazide to produce the desired properties. Placement of an adsorption-promoting moiety (such as the thioureido group) either on the meta-position of the phenyl ring (compound II-3), directly onto the oxalyl moiety (compound II-5), or indirectly onto the oxalyl moiety (compound II-6) converts these compounds into desensitizing agents.

SUMMARY OF THE INVENTION

An object of the present invention is to provide novel contrast-enhancing agents that can be used in photographic elements to produce high-contrast negative images.

Another object of the present invention is to provide a method by which high-contrast silver halide photographic elements can be formed using a stable developer.

A third object of the present invention is to provide a photographic elements that will generate high quality screen dots.

A fourth object of the present invention is to provide a photographic elements that will possess a sufficiently wide screen range so as to accurately reproduce, in dot form, the contrast range of the original subject.

Yet another object of the present invention is to provide a photographic element containing less pepper grain.

Still another object of the present invention is to provide a method such that the above objects can be obtained with little variation in sensitivity and unevenness of development due to changes in processing conditions (such as stirring rate) or equipment, or changes in processing temperature.

Other objects of the present invention will become apparent from the following detailed description, examples, and claims.

One aspect of the present invention relates to a method of forming a photographic image which comprises providing a developer solution, said solution containing a dihydroxybenzene derivative, a substituted benzotriazole, a sulfite preservative and an amine compound; processing in said solution a silver halide photographic light-sensitive material said material comprising a support having thereon at least one surface-latent image type silver halide emulsion layer, and containing in at least one layer selected from a silver halide emulsion layer and another hydrophilic colloid layer a substituted oxalyl compound represented by the formula (I):

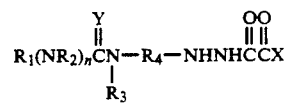

Wherein:
$X = -NR_5R_6$, or $-OR_7$;
$R_1$ and $R_2$ are independently hydrogen, alkyl, haloalkyl, hydroxyalkyl alkoxyalkyl, alkylaminoalkyl or arylalkyl having up to 18 carbons; cycloalkyl; phenyl or naphthyl; alkylphenyl, cyanophenyl, halophenyl or alkoxyphenyl substituents;
$R_3$ is hydrogen, benzyl, alkoxybenzyl, halobenzyl or alkylbenzyl, except if neither $R_1$ nor $R_2$ are hydrogen then $R_3$ must be hydrogen;
$R_4$ is a substituted or unsubstituted divalent aromatic group;
$R_5$, $R_6$ and $R_7$ are independently hydrogen, alkyl, hydroxyalkyl, haloalkyl, alkoxyalkyl, alkylaminoalkyl, acylaminoalkyl, aminoalkyl or phenylalkyl having up to 12 carbons; a cycloalkyl substituent; phenyl or naphthyl; an alkylphenyl, cyanophenyl, halophenyl or alkoxyphenyl substituent;
$R_1$ and $R_3$ or $R_1$ and $R_2$ can be linked to form a heterocyclic ring system containing three to ten carbon atoms;
$R_5$ and $R_6$ can be linked to form a heterocyclic ring system containing 3–10 atoms; Y is an oxygen or sulfur atom; $n = 0,1$ but if Y is sulfur then $n = 1$.

Another aspect of the present invention relates to the above-identified compounds and their use as high quality dot-producing agents of the class described above.

Yet another aspect of the present invention relates to a silver halide photographic emulsion comprising a binder, radiation-sensitive silver halide grains, and a dot-promoting amount of at least one of the above compounds as a fogging agent.

Another aspect of the invention relates to a radiation-sensitive photographic element comprising a support having thereon a layer comprising the above-described silver halide photographic emulsion.

Still another aspect of the invention relates to a method for the formation of high quality dot images via the processing of the described photographic element in a developing chemistry containing a composition of a dihydroxybenzene derivative, a substituted benzotriazole, a sulfite preservative and an amine compound.

DETAILED DESCRIPTION OF THE PREFERRED EMBODIMENT

In the general formula (I) described above, $R_1$ represents a hydrogen atom, an unsubstituted or substituted alkyl group (suitable substituents include halo, alkoxy, alkylamino or aryl), an unsubstituted or substituted aryl group (suitable substituents include alkyl, cyano, halo or alkoxy), a cycloalkyl group or an arylsulfonyl group. The total number of carbon atoms in $R_1$ can be up to 18 but, preferably, should be less than 12. Most preferably, $R_1$ is unsubstituted alkyl or cycloalkyl containing 1-6 carbon atoms.

$R_2$ is independently chosen from the group representing $R_1$; preferably, however, the total number of carbon atoms between $R_1$ and $R_2$ should not exceed 12.

$R_3$ represents a hydrogen atom, an unsubstituted or substituted benzyl group (suitable substituents include alkoxy, halo or alkyl). If neither $R_1$ nor $R_2$ is hydrogen, then $R_3$ must be hydrogen. Most preferably, $R_3$ is hydrogen.

Y represents an oxygen or a sulfur atom. In the preferred case, Y is a sulfur atom.

$n=0$ or 1. If Y is a sulfur atom then $n=1$. In the most preferred case $n=1$.

$R_4$ represents either an unsubstituted or substituted divalent aromatic group. Suitable substituents include alkyl, alkoxy, halo, or acylamino functionalities. In the most preferred case $R_4$ is phenylene with the thioamido or amido group in the ortho- or para- position relative to the hydrazino group. Furthermore, it is preferred that any suitable substituent as described herein be attached at the remaining, unoccupied ortho- or para-position relative to the hydrazine group.

$R_5$ represents either a hydrogen atom, an unsubstituted or substituted alkyl group (suitable substituents include hydroxy, halo, alkoxy, alkylamino, acylamino, amino and aryl), a cycloalkyl group, an unsubstituted or substituted aryl group (suitable substituents include alkyl, cyano, halo or alkoxy) or an unsubstituted or substituted amine. The total number of carbon atoms in $R_5$ should be up to 12. Preferably, $R_5$ is alkyl, cycloalkyl, dialkylaminoalkyl or acylaminoalkyl each containing 1-6 carbon atoms.

$R_6$ and $R_7$ are independently chosen from the group representing $R_5$; preferably, however, the total number of carbon atoms between $R_5$ and $R_6$ should not exceed 12. In addition, $R_5$ and $R_6$ preferably do not contain amino functionalities that are directly linked to the nitrogen atom of X.

Furthermore, $R_5$ and $R_6$ can be linked to form a heterocyclic ring system containing 3-10 atoms.

Additionally, either $R_1$ and $R_3$ or $R_1$ and $R_2$ can be linked to form a heterocyclic ring system containing 3-10 carbon atoms.

The preferred compounds represented by the general formula (I) are those represented by the general formula (Ia).

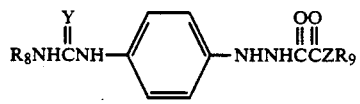
(Ia)

In this formula, $Y=S$ or O; $Z=O$ or NH; $R_8$ and $R_9$ have the same meaning as $R_1$ and $R_5$ respectively for the above described general formula (I). Most preferably $R_8$ is ethyl, n-butyl or cyclohexyl, $R_9$ is hydrogen, methyl, ethyl, dimethylaminoethyl or acetylaminoethyl, $Z=NH$, and $Y=S$.

Specific examples of the compounds represented by the general formula (I) are given below in Table I, but the present invention is not limited to these examples.

TABLE 1

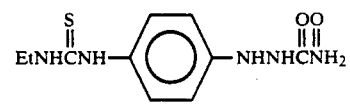 I-1

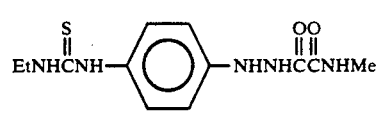 I-2

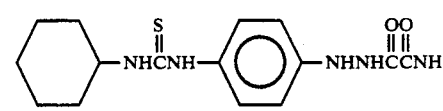 I-3

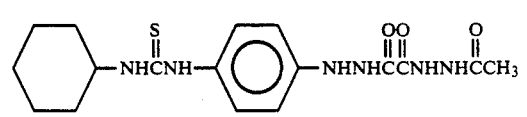 I-4

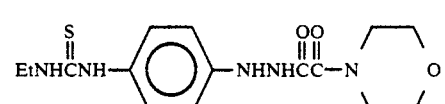 I-5

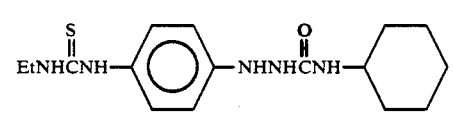 I-6

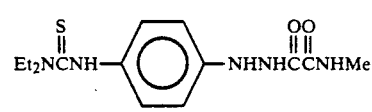 I-7

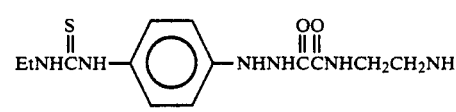 I-8

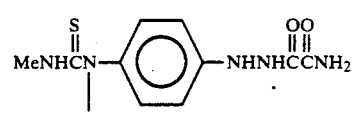 I-9

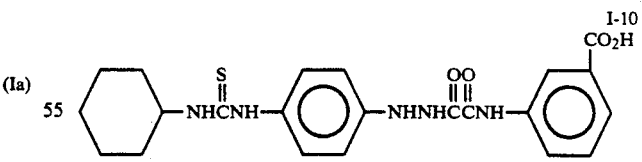 I-10

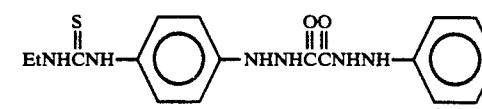 I-11

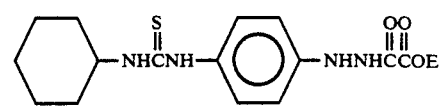 I-12

TABLE 1-continued
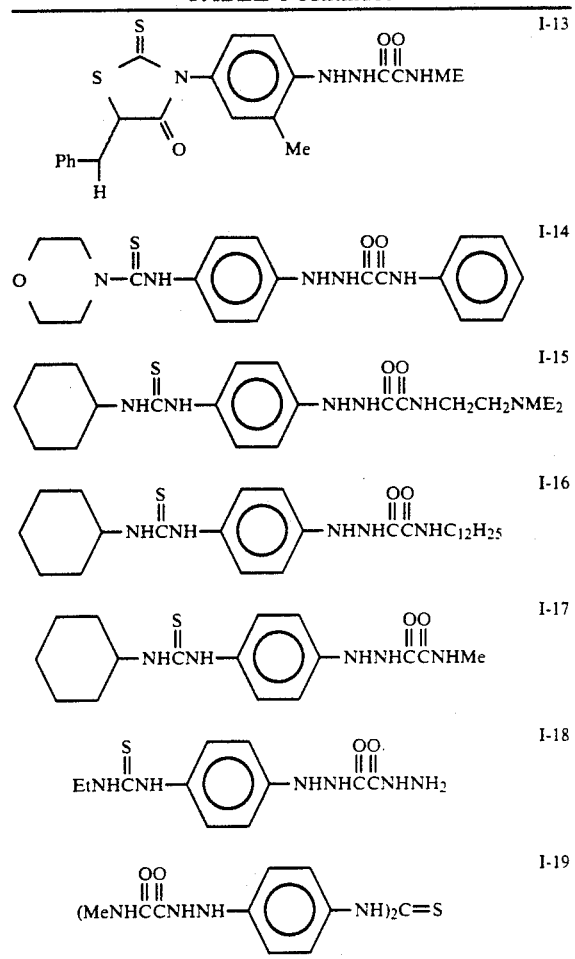
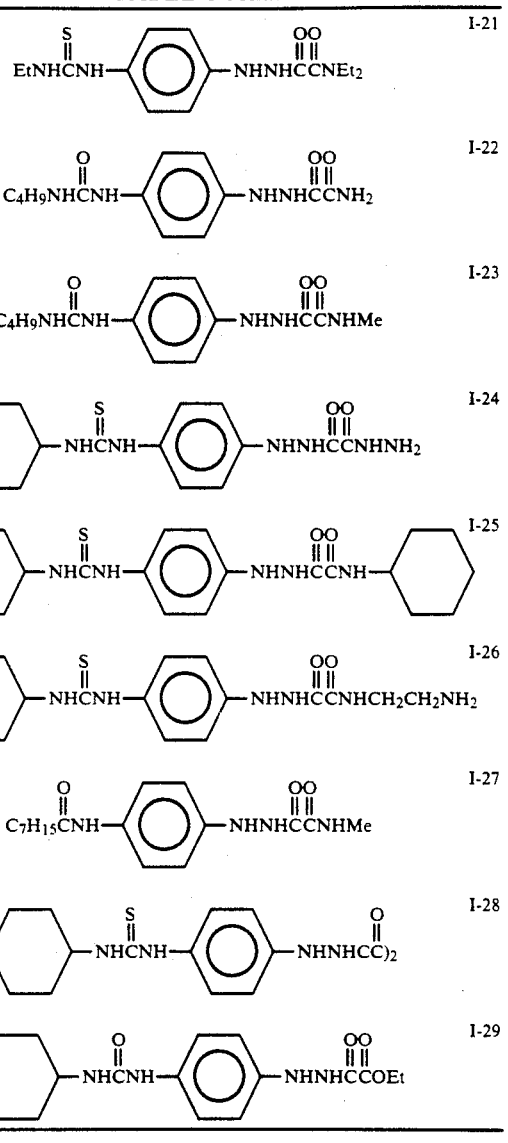
The compounds in Table II, below, are set forth here for comparison:
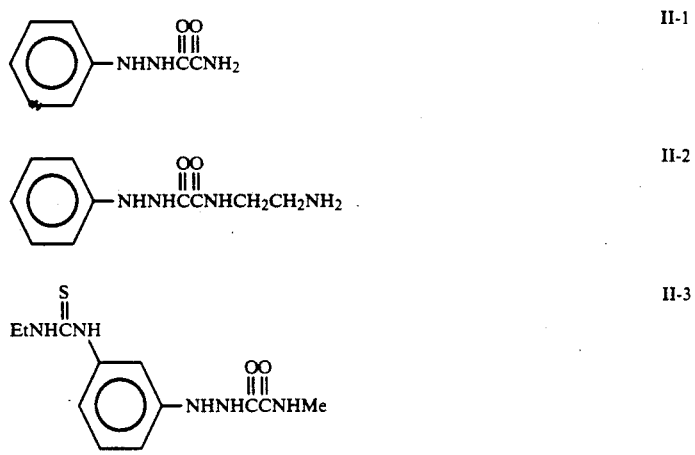

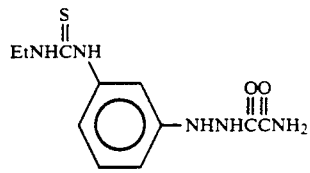
II-4

II-5

II-6

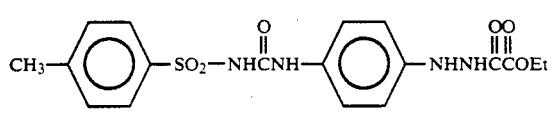
II-7

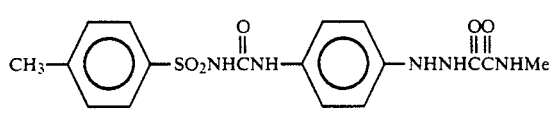
II-8

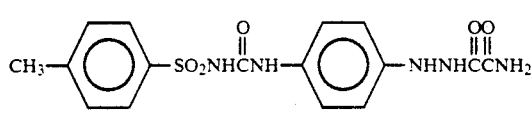
II-9

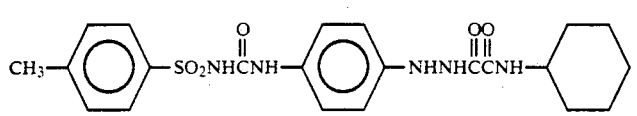
II-10

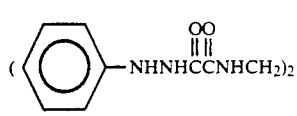
II-11

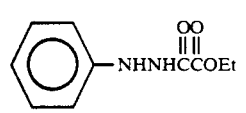
II-12

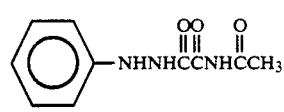
II-13

II-14

II-15

The amount of the compound of formula (I) added to the silver halide emulsion layer of hydrophilic colloidal layer(s) is such that the compound does not appreciably function as a developer. Typically, amounts from $10^{-9}$ to $5 \times 10^{-2}$ moles/mole Ag and preferably about $10^{-5}$ to $5 \times 10^{-3}$ mole/mole Ag are used.

The compound can be incorporated in a silver halide emulsion used in the photographic element. Alternatively, the ethanedioic acid hydrazide compound can be present in a hydrophilic colloid layer of the photographic element, preferably a hydrophilic colloid layer which is coated to be contiguously adjacent to the emulsion layer in which the effects of the compound are desired. The compound of the present invention can, of course, be present in the photographic element distributed between or among the emulsion and hydrophilic colloid layers, such as undercoating layers, interlayers and overcoating layers.

The ethanedioic acid hydrazide compounds of the present invention are employed in combination with negative-working photographic emulsions comprising radiation-sensitive silver halide grains capable of forming a surface latent image, and a binder. The silver halide emulsions include the high-chloride emulsions conventionally employed in forming lith photographic elements as well as silver bromide and silver bromiodide emulsions, which are recognized in the art to be capable of attaining higher photographic speeds. Generally, the iodide content of the silver halide emulsions is less than about 10 mole percent silver iodide, based on the total amount of silver halide.

The compound of formula (I) can be incorporated in the photographic element by common techniques used for the addition of additives to photographic emulsions. The compound is typically dissolved in a solvent selected from organic solvents compatible with water, such as alcohols, glycols, ketones, esters, amides, and the like which exert no adverse influences on the photographic characteristics, and the solution is added to the photographic element. Preferred solvents include dimethylformamide (DMF), dimethylsulfoxide (DMSO) and N-methyl-2-pyrrolidinone (NMP).

Alternatively, the compound of formula (I) can be added to the emulsion in an oil dispersion by known methods used when water-insoluble (so-called oil soluble) couplers are added to emulsions. Preferred oils include N-butyl acetanilide, N-methyl formanilide and N,N-diethyl-m-toluamide. These oils are all commercially available. Ultrasound can be employed to dissolve marginally soluble ethanedioic acid hydrazides. These solutions or dispersions can be added to the emulsion at any stage subsequent to the precipitation and washing steps. Preferably, these agents should be added during chemical ripening or just prior to coating.

Gelatin is advantageously used as a binder or protective colloid in the photographic emulsion, but other hydrophilic colloids can also be used. For example, gelatin derivatives, graft polymers of gelatin with other high molecular weight materials, proteins such as albumin or casein. Cellulose derivatives such as hydroxyethyl cellulose, carboxymethyl cellulose or cellulose sulfate, saccharide derivatives such as sodium alginate or starch derivatives, various synthetic hydrophilic high molecular weight materials such as homopolymers or copolymers, e.g., polyvinyl alcohol, polyvinyl alcohol (partial acetal), poly-N-vinyl pyrrolidone, polyacrylic acid, polymethacrylic acid, polyacrylamide, polyvinyl imidazole, polyvinyl pyrazole, etc., can be used. Polyglycoside dextrans are preferred.

Lime-processed gelatin and acid-processed gelatin can be used as the gelatin. Hydrolysed or enzyme-decomposed gelatin can also be used. Suitable gelatin derivatives are prepared by reacting gelatin with various compounds such as acid halides, acid anhydrides, isocyanates, bromoacetic acid, alkanesultones, vinylsulfonamides, maleinimide compounds, polyalkylene oxides or epoxy compounds and, preferably, with phthalic anhydride or succinic anhydride. Specific examples of these gelatin derivatives are described in e.g., U.S. Pat. Nos. 2,614,928, 3,132,945, 3,186,846 and 1,005,784, all incorporated by reference.

Examples of suitable gelatin graft polymers include those prepared by grafting a homopolymer or a copolymer of a vinylic monomer such as acrylic acid, methacrylic acid, the derivatives thereof (such as the esters or the amides thereof), acrylonitrile or styrene to gelatin. In particular, graft polymers prepared from polymers which are compatible with gelatin to some degree, such as those of acrylic acid, methacrylamide or a hydroxyalkyl methacrylate are preferred. Examples of those polymers are described in, e.g., U.S. Pat. Nos. 2,763,625, 2,831,767 and 2,956,884, etc. Typical synthetic hydrophilic high molecular weight materials are described in, e.g., German Patent Application (OLS) 2,312,708, U.S. Pat. Nos. 3,620,751 and 3,879,205, all incorporated by reference.

The photographic emulsion used in this invention can be prepared using the well-known methods described in, e.g., P. Glafkides, Chimie et Physique Photographique, Paul Montel, Paris (1967), G. F. Duffin, Photographic Emulsion Chemistry, The Focal Press, London (1966), V. L. Zelikman et al., Making and Coating Photographic Emulsions, the Focal Press, London (1964), all incorporated by reference. These methods include the acid method, the neutral method, the ammonia method and others. Moreover, a soluble silver salt can be reacted with a soluble halogen salt using any of the single jet method, the double jet method and a combination thereof. The method of forming grains in the presence of an excess of silver ions (the so-called "reverse mixing method") can also be used. The "controlled double jet method" (also called "controlled diffusion method") is preferred. According to this method, the pAg of the liquid phase (in which the silver halide is to be produced) is kept constant. This method can provide silver halide emulsions having a regular crystal form and an almost uniform grain size.

The silver halide grains in the photographic emulsion used in this invention can have a relatively wide grain size distribution, but a narrow grain size distribution is preferred. In particular, the size of the silver halide grains amounting to 90% of the total, based on the weight or number of the grains, is preferably within +40% of the average grain size (such an emulsion is usually called a monodispersed emulsion).

The individual reactants can be added to the reaction vessel through surface or sub-surface delivery tubes by gravity feed or by delivery apparatus for maintaining control of the pH and/or pAg of the reaction vessel contents, as illustrated by Culhane et al U.S. Pat. No. 3,821,002, and Oliver U.S. Pat. No. 3,031,304, all incorporated by reference. In order to obtain rapid distribution of the reactants within the reaction vessel, specially constructed mixing devices can be employed, as illustrated by Audran U.S. Pat. No. 2,996,287, McCrossen et al U.S. Pat. No. 3,342,605, Frame et al U.S. Pat. No. 3,415,650, Porter et al U.S. Pat. No. 3,785,777, Saito et al German OLS 2,556,885 and Sato et al German OLS 2,555,364, all incorporated by reference. An enclosed reaction vessel can be employed to receive and mix reactants upstream of the main reaction vessel, as illustrated by Forster et al U.S. Pat. No. 3,897,935 and Posse et al U.S. Pat. No. 3,790,386.

The grain size distribution of the silver halide emulsions can be controlled by silver halide grain separation techniques or by blending silver halide emulsions of differing grain sizes. The emulsions can include ammoniacal emulsions, as illustrated by Glafkides, Photographic Chemistry, Vol. 1, Fountain Press, London, 1958, pp. 365-368 and pp. 301-304; thiocyanate ripened emulsions, as illustrated by Illingsworth U.S. Pat. No. 3,320,069; thioether ripened emulsions, as illustrated by McBride U.S. Pat. No. 3,271,157, Jones U.S. Pat. No. 3,574,628 and Rosecrants et al U.S. Pat. No. 3,737,313 or emulsions containing weak silver halide solvents, such as ammonium salts, as illustrated by Perignon U.S. Pat. No. 3,784,381 and Research Disclosure, Vol. 134, June 1975, Item 13452, all incorporated by reference. The method using ammonium salts is preferred.

The crystal form of the silver halide grains in the photographic emulsion may be regular (such as cubic or octahedral) or irregular (such as spherical or plate-like) or a composite of these forms. The grains may comprise mixed grains having various crystal forms.

The interior and the surface layer of the silver halide grains may be different or the grains may be uniform throughout. During formation or physical ripening of the grains, cadmium salts, zinc salts, lead salts, thallium salts, rhodium salts or complex salts thereof, iron salts or iron complex salts, and the like can be present, as can mixtures thereof. Preferred are rhodium or iridium salts or mixtures thereof.

Two or more of silver halide emulsions which are separately prepared can be mixed and then used, if desired.

After the formation of the precipitates or after physical ripening, the soluble salts are usually removed from the emulsion. For this purpose, the well-known noodle washing method may be used. Alternatively, the flocculation method may be used. This method employs an inorganic salt having a polyvalent anion such as sodium sulfate, an anionic surface active agent, an anionic polymer (such as polystyrene sulfonic acid) or a gelatin derivative (such as an aliphatic acylated gelatin, an aromatic acylated gelatin or an aromatic carbamoylated gelatin). The removal of the soluble salts may be omitted, if desired.

Although the silver halide emulsions used in the present invention do not need to be chemically sensitized, chemically sensitized silver halide emulsions are preferred. Processes for chemical sensitization, of the silver halide emulsions which can be used include known sulfur sensitization, reduction sensitization and noble metal sensitization processes. In addition to sulfur sensitization, selenium, tellurium, rhenium or phosphorus sensitizers or combinations of these sensitizers can be used. Chemical ripening can be performed at pAg levels of from 5 to 10, pH levels of from 5 to 8 and at temperatures from 30° to 80° C.

These processes are described in references such as P. Glafkides, Chimie et Physique Photographique, Paul Montel, Paris (1967) or Zelikmann, Making and Coating Photographic Emulsions, The Focal Press, London (1964) or H. Frieser, Die Gundlagen der Photographischen Prozesse mit Silberhalogeniden, Akademische Verlagsgesellschaft (1968). The disclosure of these references is incorporated by reference. In the noble metal sensitization processes, a gold sensitization process is a typical process where gold compounds or mainly gold complexes are used.

Complexes of noble group VIII metals other than gold, such as those of platinum, palladium, osmium or iridium, etc. can also be used. A reduction sensitization process may be used if the process does not generate fog to a degree that causes practical difficulties. A particularly preferred chemical sensitization process for the present invention is the use of a sulfur sensitization process.

Examples of sulfur sensitizing agents which can be used include not only sulfur compounds present in the gelatin per se, but also various sulfur compound such as thiosulfates, thioureas, thiazoles or rhodanines, etc. Examples of suitable sulfur compounds are described in U.S. Pat. Nos. 1,574,994, 2,410,689, 2,278,947, 2,728,668 and 3,656,955, all incorporated by reference. Typical examples of suitable reduction-sensitizing agents include stannous salts, amines, formamidine sulfinic acid and silane compounds, methyldichlorosilane, hydrazine derivatives, aminoboranes, thiourea dioxide, hydrogen, cyanoborohydrides, etc. Reduction sensitization can also be obtained by low pAg (less than 5) or high pH (greater than 8) treatment.

Specifically contemplated is the combined use of several of the aforementioned chemical ripening techniques; in particular, gold-sulfur combinations are highly preferred.

A photographic material used in this invention may contain an anti-foggant. Examples of anti-foggants which can be advantageously used for the photographic material used in this invention are 1,2,4-triazole compounds substituted with a mercapto group at the 3-position, benzotriazole compounds, 2-mercaptobenzimidazole compounds (which do not contain a nitro group), 2-mercaptopyrimidines, 2-mercaptothiazoles, 2-mercaptobenzothiazoles, benzothiazolium compounds (such as N-alkylbenzothiazolium halides, nitrobenzindazole, substituted triazaindolizines (tetraazaindenes) or N-allylbenzothiazolium halides), and 2-mercapto-1,3,4-thiazoles. Antifoggants which are not effective when used alone, such as 6-nitrobenzimidazole, however, can be used in combination with any of the above advantageous antifoggants.

It has been observed that both fog reduction and an increase in contrast are obtainable by employing benzotriazole antifoggants. When the benzotriazole is located in the photographic element concentrations of $10^{-4}$ to $10^{-1}$, preferably $10^{-3}$ to $3\times10^{-2}$, mole per mole of silver are employed.

Useful benzotriazoles can be chosen from among conventional benzotriazole antifoggants, such as those disclosed by Land U.S. Pat. No. 2,704,721 and Rogers et al U.S. Pat. No. 3,265,498, both incorporated by reference. The preferred benzotriazoles for use in this invention are benzotriazole (that is, the unsubstituted benzotriazole compound), halo-substituted benzotriazoles (e.g., 5-chlorobenzotriazole, 4-bromobenzotriazole and 4-chlorobenzotriazole) and alkyl-substituted benzotriazoles wherein the alkyl moiety contains from about 1 to 12 carbon atoms (e.g., 5-methylbenzotriazole). 5-methyl benzotriazole is most preferred. The use of 5-methylbenzotriazole as an antifoggant is illustrated by Baldassari et al U.S. Pat. No. 3,925,086, incorporated by reference.

The effect of this invention is enhanced even more by adding a small amount of an iodide salt (such as potassium iodide) to the emulsion after the formation of the grains, before chemical ripening, after chemical ripening, or before coating. A suitable amount of iodide ranges from about $10^{-4}$ to about $10^{-2}$ mol/mol Ag.

The photographic emulsions used in this invention can be spectrally sensitized with methine or other dyes. Suitable sensitizing dyes include cyanine dyes, merocyanine dyes, complex cyanine dyes, hemicyanine dyes, styryl dyes and hemioxonol dyes. Particularly useful dyes are cyanine dyes, merocyanine dyes and complex merocyanine dyes. These dyes can contain, as a basic heterocyclic nucleus, any of the nuclei which are usually employed in cyanine dyes: a pyrroline nucleus, an oxazoline nucleus, a thiazoline nucleus, a pyrrole nucleus, an oxazole nucleus, a thiazole nucleus, a selenazole nucleus, an imidazole nucleus, a tetrazole nucleus, a pyridine nucleus and the like; one of the above-described nuclei condensed with an alicyclic hydrocarbon ring; and one of the above-described nuclei condensed with an aromatic hydrocarbon ring, such as an indolenine nucleus, a benzindolenine nucleus, an indole nucleus, a benzoxazole nucleus, a naphthoxazole nucleus, a benzothiazole nucleus, a naphthothiazole nucleus, a benzoselenazole nucleus, a benzimidazole nucleus and a quinoline nucleus. The carbon atoms of the above-described nuclei may be substituted.

The merocyanine dyes or complex merocyanine dyes can contain, as a nucleus having a ketomethylene structure, a 5-to 6-membered heterocyclic nucleus such as a pyrazolin-5-one nucleus, a thiohydantoin nucleus, a 2-thiooxazolidin-2,4-dione nucleus, a thiazolidin-2,4-dione nucleus, a rhodanine nucleus or a thiobarbituric acid nucleus.

Useful sensitizing dyes are those described in, e.g., German Pat. No. 929,080, U.S. Pat. Nos. 2,231,658, 2,493,748, 2,503,776, 2,519,001, 2,912,329, 3,656,959, 3,672,897 and 3,694,217, and British Pat. No. 1,242,588, all incorporated by reference.

These sensitizing dyes may be used individually or in combination. A combination of sensitizing dyes is often employed particularly for the purpose of supersensitization. Typical examples of such combinations are described in, e.g., U.S. Pat. Nos. 2,688,545, 2,977,229, 3,397,060, 3,522,052, 3,527,641, 3,617,293, 3,628,964, 3,666,480, 3,679,428, 3,703,377, 3,769,301, 3,814,609 and 3,837,862, and British Pat. No. 1,344,281, all incorporated by reference. Preferred sensitizing dye combinations are mixtures of cyanine and merocyanine dyes that orthochromatically sensitize at wavelengths between 400 and 580 nm.

The sensitizing dyes may be present in the emulsion together with dyes which themselves do not have any spectral sensitizing effects but exhibit a supersensitizing effect when used in combination, or with materials which do not substantially absorb visible light but exhibit a supersensitizing effect when used in combination. For example, aminostilbene compounds substituted with a nitrogen-containing heterocyclic ring group (e.g., those described in U.S. Pat. Nos. 2,933,390 and 3,635,721), aromatic organic acid formaldehyde condensates (e.g., those described in U.S. Pat. No. 3,743,510), azaindene compounds, and the like, can be present. The combinations described in U.S. Pat. Nos. 3,615,613, 3,615,641, 3,617,295 and 3,635,721 are particularly useful. (The disclosure of all patents mentioned in this paragraph is incorporated by reference.)

A water-soluble dye may be present in any of the hydrophilic colloid layers of the photographic light-sensitive material used in this invention, for example, as a filter dye or for prevention of light scattering, or for antihalation. Examples of these dyes include oxonol dyes, hemioxonol dyes, styryl dyes, merocyanine dyes, cyanine dyes and azo dyes. Of these dyes, oxonol dyes, hemioxonol dyes and merocyanine dyes are particularly useful. Specific examples of dyes which can be used are those described in British Pat. Nos. 584,609 and 1,177,429, and U.S. Pat. Nos. 2,274,782, 2,533,472, 2,956,879, 3,148,187, 3,177,078, 3,247,127, 3,540,887, 3,575,704, 3,653,905 and 3,718,472, all incorporated by reference.

An inorganic or organic hardener may be present in any of the hydrophilic colloid layers in the light-sensitive material used in this invention. These hardeners include, for example, chromium salts (such as chrome alum or chromium acetate), aldehydes (such as formaldehyde, glyoxal or glutaraldehyde), N-methylol compounds (such as dimethylolurea or methyloldimethylhydantoin), dioxane derivatives (such as 2,3-dihydroxydioxane), active vinyl compounds (such as 1,3,5-triacryloyl-hexahydro-s-triazine or bis(vinylsulfonyl)methyl ether), active halogen compounds (such as 2,4-dichloro-6-hydroxy-s-triazine), mucohalic acids (such as mucochloric acid or mucophenoxychloric acid), isooxazoles, dialdehyde starch, 2-chloro-6-hydroxytriazinylated gelatin and the like can be used individually or in combination. Specific examples of these compounds are described, e.g., U.S. Pat. Nos. 1,870,354, 2,080,019, 2,726,162, 2,870,013, 2,983,611, 2,992,109, 3,047,394, 3,057,723, 3,103,437, 3,321,313, 3,325,287, 3,362,827, 3,539,664 and 3,543,292, British Pat. Nos. 676,628, 825,544 and 1,270,578, and German Pat. Nos. 872,153 and 1,090,427, all incorporated by reference. A preferred hardener is one that will not cause reduction-sensitization (formaldehyde, for example, should be avoided). An example of a preferred hardener is dichlorohydroxytriazine.

The light-sensitive material of this invention may contain various known surface active agents for various purposes, e.g., as a coating aid, for preventing the generation of static charges, improving slip characteristics, improving emulsion dispersion, preventing adhesion, improving photographic characteristics (e.g., accelerating development, increasing contrast, sensitization), etc.

Examples of suitable surfactants are: nonionic surface active agents such as saponin (steroids), alkylene oxide derivatives (such as polyethylene glycol, polyethylene glycol/polypropylene glycol condensates, polyethylene glycol alkyl or alkylaryl ethers, polyethylene glycol esters, polyethylene glycol sorbitan esters, polyalkylene glycol alkylamines or amides or silicone/polyethylene oxide adducts), glycidol derivatives (such as alkenylsuccinic acid polyglycerides or alkylphenol polyglycerides), aliphatic esters of polyhydric alcohols, alkyl esters of sucrose, urethanes or ethers; anionic surface active agents containing an acidic group such as a carboxy group, a sulfo group, a phospho group, a sulfuric acid ester group or a phosphoric acid ester group, such as triterpenoid type saponin, alkylcarboxylates, alkylsulfonates, alkylbenzenesulfonates, alkylnaphthalenesulfonates, alkyl sulfuric acid esters, alkyl phosphoric acid esters, N-acyl-N-alkyltaurines, sulfosuccinates, sulfoalkylpolyoxyethylene alkylphenyl ethers or polyoxyethylene alkylphosphates; amphoteric surface active agents such as amino acids, aminoalkylsulfonic acids, aminoalkylsulfuric acid esters, aminoalkylphosphoric acid esters, alkylbetaines, amineimides or amine oxides; and cationic surface active agents such as alkylamine salts, aliphatic or aromatic quaternary ammonium salts, (such as pyridinium or imidazolium salts) or phosphonium or sulfonium salts containing an aliphatic or heterocyclic ring.

Specific examples of these surface active agents are those described in, e.g., U.S. Pat. Nos. 2,240,472, 2,831,766, 3,158,484, 3,210,191, 3,294,540 and 3,507,660, British Pat. Nos. 1,012,495, 1,022,878, 1,179,290 and 1,198,450, U.S. Pat. Nos. 2,739,891, 2,823,123, 3,068,101, 3,415,649, 3,666,478 and 3,756,828, British Pat. No. 1,397,218, U.S. Pat. Nos. 3,133,816, 3,441,413, 3,475,174, 3,545,974, 3,726,683 and 3,843,368. Belgium Pat. No. 731,126, British Pat. Nos. 1,138,514, 1,159,825 and 1,374,780, and U.S. Pat. Nos. 2,271,623, 2,288,226, 2,944,900, 3,253,919, 3,671,247, 3,772,021, 3,589,906 and 3,754,924, all incorporated by reference. Specifically preferred is a mixture of saponin, nonionic surfactants such as aliphatic esters of polyhydric alcohols, and an anionic surfactant containing a sulfuric acid ester group.

The photographic emulsion used in this invention can contain a dispersion of a synthetic polymer which is insoluble or slightly soluble in water for the purpose of improving the dimensional stability, the development and the fixing and drying rates. Examples of polymers which can be used include polymers composed of one or more alkyl acrylates or methacrylates, alkoxyalkyl acrylates or methacrylates, glycidyl acrylates or methacrylates, acryl or methacrylamide, vinyl esters (for example, vinyl acetate), acrylonitrile, olefins and styrene, etc., and polymers comprising a combination of the above described monomers and acrylic acid, methacrylic acid, unsaturated dicarboxylic acids, hydroxyalkyl acrylates or methacrylates, or styrene sulfonic acid, etc. For example, those compounds described in U.S. Pat. Nos. 2,376,005, 2,739,137, 2,853,457, 3,062,674, 3,411,911, 3,488,708, 3,525,620, 3,607,290, 3,635,715 and 3,645,740, and British Pat. Nos. 1,186,699 and 1,307,373, all incorporated by reference, can be used. A suitable amount of the polymer ranges from about 20 to 80% by weight based on the total weight of the binders. Since high-contrast emulsions such as that used in this invention are suitable for the reproduction of line drawings and the dimensional stability is of importance for such a purpose, it is preferred to use the above-described polymer dispersion.

In addition to the components of the photographic emulsions and other hydrophilic colloid layers described above, it is appreciated that other conventional agents compatible with obtaining relatively high contrast images can be present. For example, the photographic elements can contain developing agents (described below in connection with the processing steps), development modifiers, plasticizers and lubricants, coating aids, antistatic materials, matting agents, brighteners and color materials, these conventional materials being illustrated in Paragraphs V, VII, XI, XII, and XVI of Research Disclosure, December 1978 Item 17643, all incorporated by reference. Preferably, the photographic emulsion also contains anti-ageing agents, useful to prolong the shelf life of the emulsion. Suitable anti-ageing agents (especially for rhodium-doped emulsions) include polyhydroxyspiro-bis-indane as disclosed in U.S. Pat. No. 4,346,167 of E. Imatomi and preferably phenidone (up to 2 g/kg of emulsion) as disclosed in U.S. Pat. No. 2,751,297 of G. Hood.

In forming the photographic elements, the layers can be applied on photographic supports by various procedures, including immersion or kip coating, roller coating, reverse roll coating, air knife coating, doctor blade coating, gravure coating, spray coating, extrusion coating, bead coating, stretch-flow coating and curtain coating. High speed coating using a pressure differential is illustrated by Beguin U.S. Pat. No. 2,681,294. Controlled variation in the pressure differential to facilitate coating starts is illustrated by Johnson U.S. Pat. No. 3,220,877 and to minimize splicing disruptions is illustrated by Fowble U.S. Pat. No. 3,916,043. Coating at reduced pressures to accelerate drying is illustrated by Beck U.S. Pat. No. 2,815,307. Very high speed curtain coating is illustrated by Greiller U.S. Pat. No. 3,632,374. Two or more layers can be coated simultaneously, as illustrated by Russell U.S. Pat. No. 2,761,791, Wynn U.S. Pat. No. 2,941,898, Miller et al U.S. Pat. No. 3,206,323, Bacon et al U.S. Pat. No. 3,425,857, Hughes U.S. Pat. No. 3,508,947, Herzhoff et al U.K. Patent 1,208,809, Herzhoff et al U.S. Pat. No. 3,645,773 and Dittman et al U.S. Pat. No. 4,001,024. In simultaneous multilayer coating varied coating hoppers can be used, as illustrated by Russell et al U.S. Pat. No. 2,761,417, Russell U.S. Pat. Nos. 2,761,418 and 3,474,758, Mercier et al U.S. Pat. No. 2,761,419, Wright U.S. Pat. No. 2,975,754, Padday U.S. Pat. No. 3,005,440, Mercier U.S. Pat. No. 3,627,564, Timson U.S. Pat. Nos. 3,749,053 and 3,958,532, Jackson U.S. Pat. No. 3,933,019 and Jackson et al U.S. Pat. No. 3,996,885. Silver halide layers can also be coated by vacuum evaporation, as illustrated by Lu Valle et at U.S. Pat. Nos. 3,219,444 and 3,219,451. (The disclosures of all of the patents in this paragraph are incorporated by reference.)

The photographic emulsions are coated on conventional supports which do not undergo serious dimensional changes during processing. Typical suitable supports are a cellulose acetate film, a polystyrene film, a polyethylene terephthalate film, a polycarbonate film, a laminate thereof, paper, baryta paper, paper coated on laminated with a hydrophobic polymer such as polyethylene, polypropylene, etc. as are commonly used for photographic light-sensitive materials. Transparent supports can be employed for certain end uses of the light-sensitive material. Also, transparent supports may be colored by adding a dye or a pigment thereto as described in J. SMPTE, 67, 296 (1958), or Cleare, U.S. Pat. No. 3,822,131 (1984), incorporated by reference. Where the adhesion between the support and the photographic emulsion layer(s) is insufficient, a subbing layer (an adhesive layer) that adheres to both the support and the photographic emulsion layer(s) can be employed. Also, in order to improve the adhesion, the surface of the support may be subjected to a preliminary processing such as corona discharge, irradiation with ultraviolet light, flame treatment, etc. A suitable coating amount of silver is about 0.5 g/m$^2$ to about 10 g/m$^2$ of the support.

The photographic elements can be imagewise exposed with various forms of energy, which encompass the ultraviolet and visible (e.g., actinic) and infrared regions of the electromagnetic spectrum as well as electron beam and beta radiation, gamma ray, X-ray, alpha particle, neutron radiation and other forms of corpuscular and wavelike radiant energy in either noncoherent (random phase) forms or coherent (in-phase) forms, as produced by lasers. Exposure can be monochromatic, orthochromatic or panchromatic. Imagewise exposures at ambient, elevated or reduced temperatures and/or pressures, including high or low intensity exposures, continuous or intermittent exposures, exposure times ranging from minutes to relatively short durations in the millisecond to microsecond range and solarizing exposures, can be employed within the useful response ranges determined by conventional sensitometric techniques, as illustrated by T. H. James, The Theory of the Photographic Process, 4th Ed., Macmillan, 1977, Chapters 4, 6, 17, 18 and 23, incorporated by reference.

The photographic light-sensitive material of this invention can be photographically processed using known methods and known processing solutions. The processing temperature usually ranges from about 18° to about 50° C., but temperatures lower than about 18° C. or higher than about 50° C. may be used. This invention is useful for the formation of an image by development in which a silver image is formed (a black-and-white photographic processing).

The developers used for black-and-white photographic processing preferably contain, as a developing agent, aminophenols (such as N-methyl-p-aminophenol), 3-pyrazolidones (such as 1-phenyl-3-pyrazolidone), 1-phenyl-3-pyrazolines, dihydroxybenzene (such as hydroquinone) and other of the aforementioned developing agents. Specific examples of the useful developing agents include hydroquinone alone, hydroquinone plus N-methyl-p-aminophenol, hydroquinone plus 1-phenyl-3-pyrazolidone, and hydroquinone plus N-methyl-p-aminophenol plus 1-phenyl-3-pyrazolidone. Moreover, the developers usually contain a known antioxidant, an alkali agent, a pH buffer or the like and, if desired, a dissolving aid, a color toning agent, a development accelerator, a surface active agent, an antifoaming agent, a water softener, a hardener, a tackifier, etc., may be present. An antifogging agent (such as an alkali metal halide or benzotriazole) may be present in the developer.

According to this invention, even when development is carried out using a developer containing more than about 0.15 mol/l of sulfite ions, a gamma of more than 8 can be obtained. The pH of the developer is preferably about 11 to about 12.3. If the pH exceeds about 12.3, the developer is unstable even when a high concentration of sulfite ions is present, and it is difficult to maintain stable photographic characteristics for more than 3 days under normal use conditions.

Fixing solutions having a composition generally employed in the art can be used in the present invention. Not only thiosulfates and thiocyanates but also organic sulfur compounds known as fixing agents can be used as fixing agents in the present invention.

Preferred examples of fixing agents which can be used in the fixing solution include water-soluble thiosulfates such as sodium thiosulfate, potassium thiosulfate, ammonium thiosulfate, etc., water-soluble thiocyanates such as sodium thiocyanate, potassium thiocyanate, ammonium thiocyanate, etc., water-soluble organic diol fixing agents containing an oxygen atom or a sulfur atom such as 3-thio-1,5-pentanediol, 3,6-dithio-1,8-octanediol, 9-oxo-3,6,12,15-tetrathio-1,17-heptadecanediol, etc., water soluble sulfur-containing organic dibasic acids and water-soluble salts thereof such as ethylenebisthioglycollic acid and the sodium salt thereof, etc., imidazolidinethiones such as methylimidazolidinethione, etc. These agents have been described in L.F.A. Mason, Photographic Processing Chemistry, pages 187 to 188, Focal Press (1966).

A particularly preferred developing system in accordance with the present invention contains a hydroquinone developing agent, a benzotriazole antifogging agent (development restrainer), diethylaminopropanediol, sodium sulfite, and a pH modifier (preferably NAOH and/or Na$_2$CO$_3$) to adjust the pH to 11.60±0.5. The most preferred developing system is set forth in Example 28.

The preferred ethanedioic acid hydrazides of the present invention are listed in Table I. Among them, the semioxamazides I-1, I-2, I-3 and I-15 are particularly preferred.

The compounds of the present invention, "I", are synthesized in accordance with the following scheme:

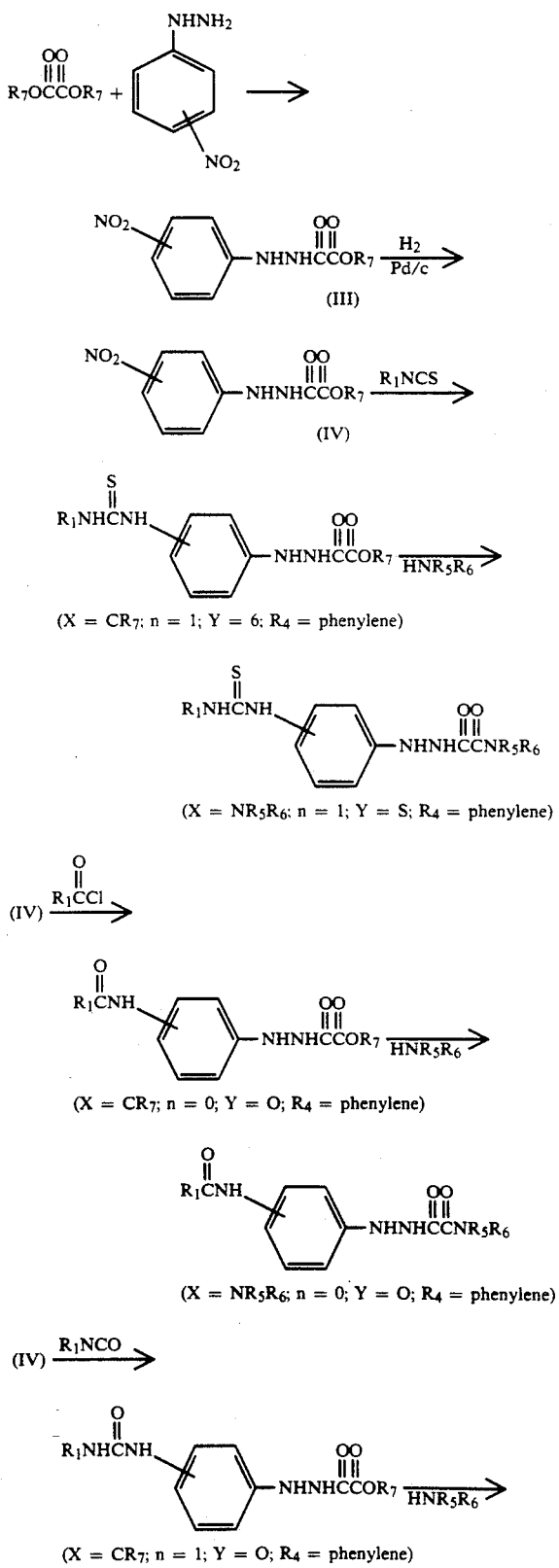

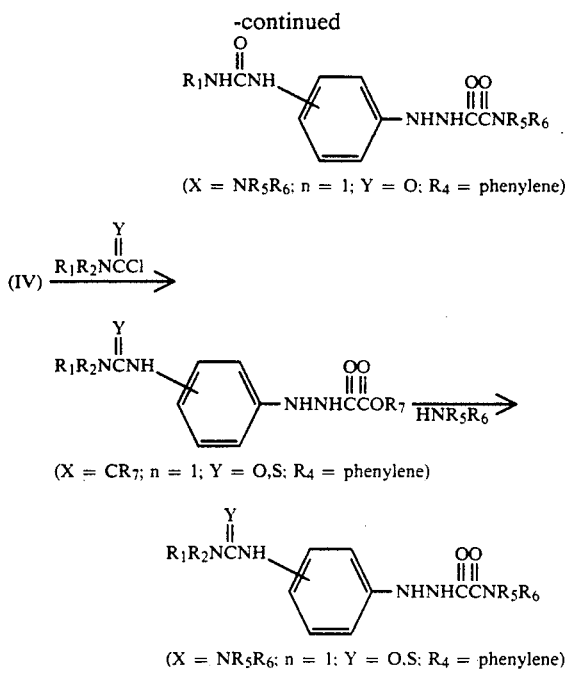

(X = NR₅R₆; n = 1; Y = O; R₄ = phenylene)

(X = CR₇; n = 1; Y = O,S; R₄ = phenylene)

(X = NR₅R₆; n = 1; Y = O,S; R₄ = phenylene)

The following examples are given to illustrate the present invention in more detail. However, the scope of the present invention is not limited to these examples.

EXAMPLE 1

Synthesis of 1-[4'-(3''-ethylthioureido)-phenyl]-5-methyl-semioxamazide (Compound I-2)

Intermediate A: ethoxalyl-2-(4'-nitrophenyl) hydrazide 4-nitrophenylhydrazine (153 gm) and 500 ml diethyl oxalate were refluxed for 90 min. Ethanol was removed as the reaction proceeded. On cooling, crystals precipitated, and were filtered off. These were washed with petroleum ether several times, and then recrystallized from hot methanol/water. The product is a tan powder (130 gm), (51%). MP 176°–7° C.

Intermediate B: ethoxalyl-2-(4'-aminophenyl) hydrazide

Intermediate B (40 gm) was added to 800 ml methanol and heated briefly over a steambath. Pd/C catalyst was added, the flask was pressurized to 50 psi, and shaken for 3 hours. The catalyst was filtered off and the filtrate concentrated by vacuum distillation. The residual solid was stirred with hot isopropanol, cooled and filtered to yield a light solid (29.3 g), (84%). MP 150°–152° C.

Intermediate C: ethoxalyl-2-(4'-[3''-ethylthioureido]phenyl)hydrazide 20 g of Intermediate B were added to 300 ml acetonitrile. 10 ml ethyl isothiocyanate was added, and the mixture heated to reflux for one hour. On chilling, solids precipitated and were collected by filtration, prior to washing with acetonitrile. A light colored solid, 16.7 g (60%) was obtained. MP 173°–4° C. (decomposition).

Compound I-2

15.5 g of Intermediate C were added to 150 ml methanol and warmed. To this was added methylamine (40 ml 40% in water) and stirred. A solid precipitated and was collected after the mixture was allowed to stand at room temperature for six hours. The product was washed with methanol to yield 8.4 g (59%). MP 228°–9° C.

| Analysis: | % C | % H | % N |
|---|---|---|---|
| Theory | 48.81 | 5.76 | 23.73 |
| Found | 48.50 | 5.48 | 23.49 |

Mass Spec m/e=295

EXAMPLES 2-7

Compounds in these examples were synthesized by following the procedure for compound I-2, but substituting appropriate amines for methylamine.

Compound I-1:
1-[4'-(3''-ethylthioureido)phenyl]semioxamazide (16.5 g Intermediate C, 5 ml ammonia) yield: 12.2 g (82%). MP 228°–229° C.

| Analysis: | % C | % H | % N |
|---|---|---|---|
| Theory | 46.60 | 5.51 | 24.83 |
| Found | 46.98 | 5.34 | 24.91 |

Mass Spec m/e=281

Compound II-11:
1-[4'-(3''-ethylthioureido)phenyl]-6-phenyl ethanedioic acid bishydrazide (3.1 gm Intermediate C, 2 ml phenylhydrazine) yield: 1.7 gm (50%). MP 236/7° C.

| Analysis: | % C | % H | % N | % S |
|---|---|---|---|---|
| Theory | 54.85 | 5.38 | 22.58 | 8.60 |
| Found | 54.67 | 5.48 | 22.46 | 8.82 |

Compound I-18: 1-[4'-(3''-ethylthioureido)phenyl] ethanedioic acid bishydrazide (3.1 g Intermediate C, 8 ml hydrazine) yield: 2.9 g (90%). MP 202/3° C.

| Analysis: | % C | % H | % N |
|---|---|---|---|
| Theory | 44.59 | 5.41 | 28.38 |
| Found | 44.38 | 5.34 | 27.68 |

Compound I-8:
1-[4'-(3''-ethylthioureido)phenyl]-5-(2-aminoethyl) semioxamazide (1.55 g Intermediate C, 0.4 g ethylenediamine) yield: 1.2 g (74%). MP 180/1° C.

| Analysis: | % C | % H | % N | % S |
|---|---|---|---|---|
| Theory | 48.13 | 6.23 | 25.90 | 9.87 |
| Found | 48.09 | 6.12 | 25.03 | 10.26 |

Compound I-6:
1-[4'-(3''-ethylthioureido)phenyl]-5-cyclohexyl semioxamazide (1 g Intermediate C, 5 ml cyclohexylamine) yield: 0.65 g (60%). MP 159°–160° C.

Compound I-21:
1-[4'-(3''-ethylthioureido)phenyl]-5,5-diethyl semioxamadize (2.4 g Intermediate C, 1.7 g diethylamine) yield: 1.2 g (44%). MP 242/3° C.

EXAMPLES 8 and 9

Intermediate D 4.5 g of Intermediate B, 75 ml acetonitrile and 3 ml butyl-isocyanate were refluxed together for one hour. An additional 1 ml butyl-isocyanate was then added and the reflux was continued for one hour. The mixture was charcoal-treated while hot, allowed to cool and the crystals were filtered off after seeding. The crystals were washed with acetonitrile and dried to yield a pale yellow powder (3.0 g), (46%). MP 174°–7° C.

Compound I-22:
1-[4'-(3''-butylureido)phenyl]semioxamazide 1.0 g Intermediate D was combined with 1 ml NH$_4$OH in 20 ml methanol and refluxed for 15 minutes. On cooling, solids precipitated and were washed with methanol to yield a pale yellow product (0.5 g), (57%). MP 275° C.

| Analysis: | % C | % H | % N |
|---|---|---|---|
| Theory | 53.24 | 6.48 | 23.89 |
| Found | 53.20 | 6.61 | 23.56 |

Compound I-23: 1-[4'(3''-butylureido)phenyl]-5-methyl semioxamazide 1.0 g of Intermediate D was combined with 1 ml aqueous methylamine in 20 ml methanol and refluxed 20 minutes. The solution was cooled, and the crystals were filtered off. On washing with methanol, a light yellow product resulted (0.77 g), (84%). MP 229°–30° C. (decomposition).

| Analysis: | % C | % H | % N |
|---|---|---|---|
| Theory | 54.72 | 6.84 | 22.80 |
| Found | 54.56 | 6.92 | 22.75 |

EXAMPLES 10 to 13

Compound II-7:
ethoxalyl-2-[4'-(3''-(p-tolyl)sulfonylureido)phenyl]hydrazide 4.5 g of Intermediate B were combined with 5.9 g toluene sulfonyl isocyanate in 50 ml acetonitrile and refluxed for 3 hours. The reaction mix was charcoal-treated, filtered, and evaporated to dryness. The solid was recrystallized from isopropanol, and the filtered solids washed sparingly with ether. A buff product resulted (6.6 g), (68%). MP 127°–8° C. (decomposition).

| Analysis: | % C | % H | % N | % S |
|---|---|---|---|---|
| Theory | 51.42 | 4.80 | 13.32 | 7.61 |
| Found | 51.02 | 5.19 | 13.34 | 7.39 |

Compound II-8:
1-[4'-(3''-(p-tolyl)sulfonylureido)phenyl]-5-methylsemioxamazide

One gram of compound II-7 was put into 15 ml ethanol and heated over a steambath. To this slurry was added 1 ml methylamine (40%) and the flask was set aside. After 30 minutes an oil separated, which redissolved on heating. This cycle was repeated several times. On cooling, a gum settled out, which was washed with petroleum ether. 20 ml acetic acid was added and the flask heated to redissolve the gum. On cooling, crystals appeared and were collected by filtration, washing with acetic acid and petroleum ether in turn. A white powder resulted (0.15 g), (19%). MP 235° C. (decomposition).

| Analysis: | % C | % H | % N | % S |
|---|---|---|---|---|
| Theory | 50.37 | 4.74 | 17.27 | 7.89 |
| Found | 50.12 | 4.94 | 17.03 | 8.05 |

Compound II-9 and II-10 were synthesized by following the procedure for Compound II-8, but substituting appropriate amines for methylamine.

Compound II-9:
1-[4'-(3''-(p-tolyl)sulfonylureido)phenyl]semioxamazide (1 g Compound II-7, 1 ml ammonium hydroxide) yield: 0.6 g (77%). MP 163/4° C.).

Compound II-10:
1-[4'-(3''-(p-tolyl)sulfonylureido)phenyl-5-cyclohexyl semioxamazide (1 g Compound II-7, 0.9 g, cyclohexylamine) yield 0.9 g (95%). MP 183/4° C.

EXAMPLES 14–21

Intermediate E:
2-ethoxalyl-(4'-[3''-cyclohexylthioureido]phenyl)hydrazide (Compound I-12)

11 g of Intermediate B were combined with 250 ml acetonitrile and heated to reflux. 9 ml cyclohexyl isothiocyanate was added dropwise, and the mixture was refluxed for an additional hour. Volume was reduced to 75 ml and the mixture cooled and filtered. Recrystallization of this solid from ethanol/water 10:1 yielded 7.8 g (45%) of a colorless solid. MP 172°–174° C. (decomposition).

Compound I-16:
1-[4'-(3''-cyclohexylthioureido)phenyl]-5-dodecyl semioxamazide 1.0 g of Intermediate E was combined in 25 ml methanol with 1.0 g dodecylamine and refluxed for 15 minutes. On cooling, solids were filtered off and washed with methanol and then with ether. A light powder resulted (1.17 g), (87%). MP 173°–5° C.

| Analysis: | % C | % H | % N | % S |
|---|---|---|---|---|
| Theory | 64.41 | 8.95 | 13.92 | 6.36 |
| Found | 64.20 | 9.24 | 14.01 | 6.23 |

Compounds in examples 15–21 were synthesized by following the procedure for Compound I-12, but substituting appropriate amines for dodecylamine.

Compound I-3:
1-[4'-(3''-cyclohexylthioureido)phenyl]semioxamazide (2.2 Intermediate E, 5 ml ammonium hydroxide) yield: 0.7 g (70%). MP 229/230° C.

Compound I-17:
1-[4'-(3''-cyclohexylthioureido)phenyl]-5-methyl semioxamazide (2 g Intermediate E, 6 ml methylamine) yield: 0.7 g (37%). MP 180°–3° C.

Compound I-24:
1-[4'-(3''-cyclohexylthioureido)phenyl]ethanedioic acid bishydrazide (1 g Intermediate E, 2 ml hydrazine) yield: 0.7 g (74%). MP 198° C.).

Compound I-25:
1-[4'-(3''-cyclohexylthioureido)phenyl]-5-cyclohexyl semioxamazide (2 g Intermediate E, 4 g cyclohexylamine) yield: 2.0 g (80%). MP 198°–200° C.

Compound I-20:
1-[4'-(3''-cyclohexylthioureido)phenyl]-5-(2'-butyl)- semioxamazide (2 g Intermediate E, 2 ml 2-butylamine) yield: 1.2 g (56%). MP 178°–180° C.).

Compound I-26:
1-[4'-(3''-cyclohexylthioureido)phenyl]-5-(2-aminoethyl)semioxamazide (3.3 g Intermediate E, 1.0 ml ethylenediamine) yield: 2.0 g (60%). MP 206°–208° C.

Compound I-4:
1-[4'-3''-cyclohexylthioureido)phenyl]-6-acetyl ethanedioic acid bishydrazide (0.9 g Compound I-26, 5 ml acetic acid, 5 ml acetic anhydride) yield: 0.65 g (65%). MP 236°–239° C.

EXAMPLES 22 and 23
Synthesis of
1-[3'-(3''-ethylthioureido)-phenyl]semioxamazide
(Compound II-4)

Intermediate F: Ethoxalyl-2-(3'-nitrophenyl)hydrazide 3.8 g of 3-nitrophenylhydrazine hydrochloride were combined with 1.8 g of sodium acetate and 6.4 g of diethyl oxalate over a steam bath. After heating for 1 hour, the mixture was allowed to cool, and the salts were filtered off. The filtrate solidified on treatment with petroleum ether, yielding light yellow solids. These were charcoaled in hot ethanol water (25:10), cooled, 10 ml additional water was added and the solids were allowed to crystallize. The filtered crystals were washed with ethanol-water (1:1). The yield was 3.0 g (59%) of light yellow crystals, MP 123°–124° C.

| Analysis: | % C | % H | % N |
|---|---|---|---|
| Theory | 47.43 | 4.35 | 16.60 |
| Found | 47.63 | 4.33 | 16.80 |

Intermediate G: 1-(3'-nitrophenyl)semioxamazide 2.5 g of Intermediate F were warmed in 25 ml methanol, prior to the addition of 2 ml NH$_4$OH. The mixture was refluxed for one hour before cooling. The resultant precipitated crystals were washed with methanol to yield a yellow powder (1.6 g), (71%). MP 226°–7° C.

Intermediate H: 1-(3'-aminophenyl)semioxamazide 1.6 g of Intermediate G were warmed in 200 ml methanol before the addition of Pd/C catalyst and hydrogenation at 50 lb hydrogen pressure. On completion of hydrogenation, precipitated solids (0.9 g) were collected.

Compound II-4:
1-[3'-(3''-ethylthioureido)phenyl]semioxamazide

Acetonitrile (25 ml) was added to Intermediate H and the mixture was refluxed. 1.0 g ethyl isothiocyanate and 10 ml DMF were added and refluxing continued for an additional hour. Insolubles were filtered off before addition of an additional 1 g ethyl isothiocyanate. A final heating for one hour was followed by solvent evaporation in vacuo. Addition of petroleum ether to the resultant oil resulted in crystals which were then washed with ether. Final product was a buff powder (0.68 g), (27%). MP 192°–4° C. (decomposition).

| Analysis: | % C | % H | % N | % S |
|---|---|---|---|---|
| Theory | 46.98 | 5.37 | 24.89 | 11.38 |
| Found | 47.10 | 5.66 | 24.02 | 20.94 |

Compound II-3:
1-[3'-(3''-ethylthioureido)phenyl]-5-methyl semioxamazide

Intermediate I:
1-(3'-nitrophenyl)-5-methylsemioxamazide 2.3 g of Intermediate F were placed in 25 ml methanol and heated to dissolve. On addition of 2 ml 40% methylamine, solids precipitated almost immediately. On cooling for one hour, solids were collected and washed with methanol to yield a yellow powder (1.9 g), (88%). MP 247°–8° C.

Intermediate J:
1-(3'-aminophenyl)-5-methylsemioxamazide 1.7 g of Intermediate I in 80 ml dimethyl formamide were hydrogenated over Pd/C catalyst at 50 psi. After 90 minutes the catalyst was filtered off and the solution used directly in the next step.

Compound II-3

3 ml of ethylisothiocyanate were added to the solution of Intermediate J in 80 ml DMF and heated as a steam bath for one hour. The DMF was removed in vacuo, and the residual oil taken up in isopropanol. After charcoal treatment, the solution was allowed to cool and the collected solids washed with cold isopropanol—pet. ether to yield a tan powder (1.4 g), (58%). MP 193°-4° C.

EXAMPLES 24-26

Compound II-2: 5-(2-aminoethyl)-1-phenylsemioxamazide 10.4 g of ethoxalyl-2-phenylhydrazide were warmed in 100 ml methanol and 4 ml ethylenediamine added. The mixture was refluxed for 30 minutes. On cooling, the filtered solids were washed with methanol to yield a white product (8.32 g), (75%). MP 183°-5° C.

Compound II-6: 5-[2'-(3''-ethylthioureido)ethyl]-1-phenyl semioxamazide 4.4 g of Compound II-2 were refluxed for 45 minutes with 3 ml ethyl isothiocyanate and filtered hot. On cooling, solids precipitated from the filtrate and were in turn filtered and washed with acetonitrile. A white product resulted (3.7 g), 60%). MP 178°-80° C.

| Analysis: | % C | % H | % N | % S |
|---|---|---|---|---|
| Theory | 50.48 | 6.15 | 22.65 | 10.36 |
| Found | 50.54 | 5.79 | 22.6 | 10.30 |

Compound II-11: 5,5'-ethylene bis(1-phenylsemioxamazide)

10.4 g of ethoxyalyl-2-phenylhydrazide were warmed in 100 ml methanol and 1.6 ml ethylene diamine were added. The mixture was refluxed 30 minutes, allowed to cool and the solids were collected. On washing with methanol, a white powder resulted (4.82 g), (50%). MP 280° C.

Compound II-5: 1-ethylaminothioxomethyl-6-phenylethanedioic acid bishydrazide 3.8 g of 1-phenyloxalylhydrazide were dissolved in 50 ml of acetonitrile and 25 ml DMF. Ethyl isocyanate, 2.5 ml, was added. The mixture was refluxed for four hours. The volume was reduced to one third in a vacuum. Water was added until the mixture was cloudy and the solids were allowed to crystallize. Yield: 2.2 g (50%). MP 209/210° C.

| Analysis: | % C | % H | % N |
|---|---|---|---|
| Theory | 46.98 | 5.34 | 24.91 |
| Found | 46.72 | 5.22 | 25.08 |

EXAMPLE 27

A gelatino-(silver chlorobromoiodide) emulsion containing approximately 90 percent chloride, 9 percent bromide and 1 percent iodide was prepared at 68° C. for 10 minutes by a standard double jet addition technique producing silver halide grains having an average size of 0.30 micron. After removal of soluble salts by a conventional method, the emulsion was chemically ripened using labile sulfur compounds at 61° C. for 70 minutes. This emulsion contained gelatin in the amount of 71.3 g per mole of silver halide.

EXAMPLE 28

A gelatino-(silver bromide) emulsion was prepared at 65° C. for 37 minutes by a controlled double jet addition technique while the pAg was maintained at 8.3. The average grain size of the silver bromide crystals was 0.27 micron with a size distribution of 16%. After removal of the soluble salts by conventional methods, the emulsion was chemically ripened using both labile sulfur and gold agents at 65° C. for 65 minutes. This surface-sensitized emulsion contained gelatin in the amount of 81.9 g per mole of silver bromide.

In the examples that follow, a comparison is made between several of the preferred semioxamazide agents as described in the present invention and structurally analogous agents. Significant parameters for comparison include:

a) Dmin=background fog optical density
b) Toe Speed=relative LogE value at OD 0.1+fog
c) Mid Speed=relative LogE value at OD 2.5+fog
d) Shoulder speed=relative LogE value at OD 3.25+fog (e.g., a speed of 70 is one stop faster than a speed of 100)
e) Dmax=maximum optical density×100
f) Gamma=(2.4×100)÷(mid speed−toe speed)
g) Pepper Level=arbitrary scale from 1 (best) to 5 (worst)
h) Dot Quality=determined for 50% dot, arbitrary scale from 1 (best) to 5 (worst)

The emulsion was exposed through an optical wedge using a tungsten light source for 2 seconds.

The exposed element was processed in a development chemistry having the following composition (EDTA is ethylenediaminetetraacetate):

| $H_2O$ | 850 ml | EDTA | 1 g |
|---|---|---|---|
| $Na_2SO_3$ | 70 g | Diethylaminopropanediol | 15 ml |
| Hydroquinone | 33 g | 50% NaOH | 23 ml |
| NaBr | 3.2 g | $Na_2CO_3$ | 45 g |
| 5-methylbenzotriazole | 0.225 g | water to 1.0 liter pH 11.60 ± 0.5 | |

Development conditions: 38° C./35 sec. in tray unless otherwise noted.

EXAMPLE 29

The emulsion described in Example 27 was split into 250 g portions. Each portion was identically prepared for coating by the addition of an orthochromatic sensitizing dye and surfactant coating aids (saponin, an ethoxylated phenol and an alkylbenzene sulfonate). Various semioxamazide derivatives were added in the amounts shown in Table B below.

The final emulsions were coated at 4.2 g silver/m² on a subbed polyester film support along with a gelatin protective layer which contained formaldehyde, surfactants and matting agents.

TABLE B

| Run # | Compound # | (mole/mole Ag) | Dmin | Rel. Shld. Speed | Gamma | Dot Quality |
|---|---|---|---|---|---|---|
| 1 | none | — | 0.06 | 100 | 5.5 | 5 |
| 2 | I-1 | $9.0 \times 10^{-5}$ | 0.08 | 62 | 14.0 | 1 |
| 3 | " | $4.5 \times 10^{-4}$ | 0.10 | 60 | 14.3 | 1 |
| 4 | I-2 | $9.0 \times 10^{-5}$ | 0.06 | 60 | 14.0 | 1 |
| 5 | " | $4.5 \times 10^{-4}$ | 0.10 | 55 | 14.5 | 1 |
| 6 | " | $9.0 \times 10^{-4}$ | 0.20 | 53 | 14.5 | 1 |
| 7 | I-4 | $1.5 \times 10^{-4}$ | 0.06 | 55 | 14.0 | 1 |
| 8 | " | $4.7 \times 10^{-4}$ | 0.08 | 63 | 14.5 | 1.5 |
| 9 | I-8 | $3.0 \times 10^{-5}$ | 0.06 | 80 | 9.0 | 2.5 |
| 10 | " | $6.0 \times 10^{-5}$ | 0.07 | 63 | 14.0 | 1.5 |
| 11 | " | $1.2 \times 10^{-4}$ | 0.09 | 55 | 14.5 | 1.5 |
| 12 | I-11 | $5.8 \times 10^{-5}$ | 0.06 | 70 | 10.0 | 2.5 |
| 13 | " | $1.2 \times 10^{-4}$ | 0.07 | 70 | 13.5 | 2 |

TABLE B-continued

| Run # | Compound # | (mole/mole Ag) | Dmin | Rel. Shld. Speed | Gamma | Dot Quality |
|---|---|---|---|---|---|---|
| 14 | " | $3.0 \times 10^{-4}$ | 0.07 | 70 | 14.0 | 1.5 |
| 15 | I-12 | $2.7 \times 10^{-5}$ | 0.06 | 77 | 7.5 | 4.5 |
| 16 | " | $5.4 \times 10^{-5}$ | 0.06 | 70 | 9.0 | 4 |
| 17 | " | $1.1 \times 10^{-4}$ | 0.07 | 62 | 13.5 | 3 |
| 18 | " | $2.7 \times 10^{-4}$ | 0.09 | 55 | 14.5 | 2.5 |
| 19 | I-15 | $2.5 \times 10^{-5}$ | 0.06 | 62 | 11.0 | 2 |
| 20 | " | $1.0 \times 10^{-4}$ | 0.09 | 47.5 | 14.5 | 1 |
| 21 | " | $2.5 \times 10^{-4}$ | 0.12 | 40 | 14.5 | 1 |
| 22 | I-20 | $2.5 \times 10^{-5}$ | 0.06 | 62.5 | 12.5 | 3 |
| 23 | " | $5.1 \times 10^{-5}$ | 0.06 | 55 | 14.0 | 2 |
| 24 | " | $1.0 \times 10^{-4}$ | 0.07 | 55 | 14.5 | 1.5 |
| 25 | " | $2.5 \times 10^{-4}$ | 0.08 | 62.5 | 14.0 | 1.5 |
| 26 | I-23 | $6.5 \times 10^{-5}$ | 0.06 | 85 | 6.5 | 3 |
| 27 | " | $2.1 \times 10^{-4}$ | 0.08 | 55 | 14.0 | 2 |
| 28 | " | $7.1 \times 10^{-4}$ | 0.12 | 47.5 | 14.5 | 2 |
| 29 | II-1 | $2.2 \times 10^{-3}$ | 0.06 | 77.5 | 10.0 | 5 |
| 30 | " | $5.5 \times 10^{-3}$ | 0.07 | 70 | 14.0 | 4 |
| 31 | " | $1.1 \times 10^{-3}$ | 0.09 | 55 | 14.5 | 4 |
| 32 | II-2 | $9.0 \times 10^{-5}$ | 0.06 | 90 | 6.5 | 5 |
| 33 | " | $1.8 \times 10^{-3}$ | 0.08 | 66 | 14.5 | 4 |
| 34 | II-3 | $1.4 \times 10^{-4}$ | 0.06 | 100 | 6.5 | 5 |
| 35 | " | $4.5 \times 10^{-4}$ | 0.06 | 110 | 6.5 | 5 |
| 36 | " | $1.5 \times 10^{-3}$ | 0.06 | 120 | 6.5 | 5 |
| 37 | II-4 | $7.1 \times 10^{-5}$ | 0.06 | 100 | 6.5 | 5 |
| 38 | " | $7.1 \times 10^{-4}$ | 0.06 | 115 | 6.5 | 5 |
| 39 | II-6 | $2.2 \times 10^{-4}$ | 0.06 | 105 | 6.5 | 5 |
| 40 | " | $7.0 \times 10^{-4}$ | 0.06 | 110 | 6.5 | 5 |
| 41 | " | $1.4 \times 10^{-3}$ | 0.06 | 120 | 6.5 | 5 |
| 42 | II-8 | $1.6 \times 10^{-4}$ | 0.06 | 100 | 6.5 | 5 |
| 43 | " | $5.0 \times 10^{-4}$ | 0.06 | 93 | 6.5 | 5 |
| 44 | " | $2.5 \times 10^{-3}$ | 0.06 | 60 | 14.5 | 4 |
| 45 | II-12 | $4.8 \times 10^{-4}$ | 0.06 | 100 | 6.5 | 5 |
| 46 | " | $2.4 \times 10^{-3}$ | 0.06 | 100 | 6.5 | 5 |
| 47 | " | $4.8 \times 10^{-3}$ | 0.06 | 100 | 6.5 | 5 |
| 48 | " | $9.6 \times 10^{-3}$ | 0.08 | 75 | 12.0 | 5 |
| 49 | II-13 | $1.5 \times 10^{-4}$ | 0.06 | 100 | 6.5 | 5 |
| 50 | " | $7.6 \times 10^{-4}$ | 0.06 | 100 | 6.5 | 5 |
| 51 | " | $1.9 \times 10^{-3}$ | 0.06 | 100 | 6.5 | 5 |
| 52 | II-14 | $3.0 \times 10^{-4}$ | 0.06 | 100 | 6.5 | 5 |
| 53 | " | $1.2 \times 10^{-3}$ | 0.06 | 110 | 6.5 | 5 |
| 54 | " | $6.1 \times 10^{-3}$ | 0.06 | 115 | 6.5 | 5 |
| 55 | II-15 | $3.8 \times 10^{-4}$ | 0.06 | 100 | 6.5 | 5 |
| 56 | " | $1.2 \times 10^{-3}$ | 0.06 | 95 | 8.0 | 5 |
| 57 | " | $3.4 \times 10^{-3}$ | 0.07 | 85 | 10.0 | 5 |

These results indicate that in order to produce a photographic image with high quality dots, it is necessary, but not sufficient, to have high contrast. Indeed, all of the preferred compounds (i.e., I-1 through I-29) have both high contrast and excellent dot quality while structurally analogous compounds (i.e., II-1 through II-15) produce high contrast/poor dots or low contrast/poor dots. The structure-activity relationship for obtaining high contrast/high quality dots is very stringent. Adsorption-promoting moieties on the phenyl ring improve dot quality to varying degrees but in the present invention it has been determined that a thioureido moiety maximizes the dot quality. This observation is unexpected in light of the prior art (U.S. Pat. No. 4,323,643) where it is claimed that, in the phenyl formyl hydrazide series, the ureido moiety produces dots of superior quality to the thioureido moiety. Additionally, our studies indicate that the position of the thioureido moiety is crucial to obtaining high contrast/high dot quality. This functionality should be attached either in the 2 or 4 position relative to the hydrazide group, in order to produce the desired effects; in all other positions, desensitization takes place.

The examples that follow compare one of the preferred semioxamazide agents of the present invention to its analog in the previously disclosed formyl hydrazide series. The photographic and sensitometric parameters discussed in Example 29 were used. In addition, processing time and temperature latitude will be taken to mean change in shoulder speed, Dmin or gamma relative to a change in either development time or temperature. The lower this ratio (i.e., small differences in speed, Dmin or gamma compared to large changes in time or temperature) the greater the processing latitude. Improvement in processing latitude for sensitized products is highly desired by the users.

EXAMPLE 30

The emulsion described in Example 27 was divided into Parts A–F weighing 250 g. Each part was identically prepared for coating by the addition of an orthochromatic sensitizing dye and coating aids such as those listed in the previous example. To each of the first three parts (A–C) 2, 4 and 6 mg of compound I-2 (1-[4-(3-ethylthioureido)phenyl]-5-methyl semioxamazide) were added. To each of the remaining three parts (D–F), 2, 4 and 6 mg of a comparison compound, specifically 2-[4-(3-cyclohexylthioureido)phenyl]-1-formyl hydrazine were added.

The final emulsions were coated at 4.4 g silver/m² on a polyester film support along with a protective overcoat layer containing gelatin, formaldehyde, surfactants and matting agents. The emulsions were exposed with a tungsten light source for 4 seconds. The chemistry described previously was used for processing in either an automatic processing unit or in a tray.

| Trial # | Part | Apparatus | (°C.) Temp | (Sec) Time | 100× Dmin | Toe | Mid | Shld | 10× Gamma | Pepper Level |
|---|---|---|---|---|---|---|---|---|---|---|
| 1 | A | Machine | 33 | 50 | 8 | 70 | 102 | 119 | 76 | 2 |
| 2 | " | " | 33 | 120 | 10 | 59 | 92 | 102 | 71 | 3 |
| 3 | " | " | 38 | 50 | 9 | 66 | 100 | 116 | 71 | 3 |
| 4 | " | " | 42 | 24 | 8 | 65 | 92 | 100 | 89 | 2 |
| 5 | " | Tray | 42 | 24 | 6 | 66 | 94 | 103 | 84 | 2 |
| 6 | " | Machine | 42 | 50 | 8 | 62 | 91 | 100 | 84 | 2 |
| 7 | " | " | 42 | 65 | 11 | 64 | 90 | 99 | 90 | 3 |
| 8 | D | " | 33 | 50 | 8 | 64 | 107 | 117 | 56 | 1 |
| 9 | " | " | 33 | 120 | 16 | 46 | 80 | 97 | 72 | 3 |
| 10 | " | " | 38 | 50 | 11 | 55 | 99 | 111 | 54 | 2 |
| 11 | " | " | 42 | 24 | 8 | 50 | 99 | 116 | 50 | 3 |
| 12 | " | Tray | 42 | 24 | 7 | 55 | 88 | 102 | 72 | 1 |
| 13 | " | Machine | 42 | 50 | 27 | 22 | 85 | 107 | 38 | 5 |
| 14 | " | " | 42 | 65 | 32 | 22 | 69 | 101 | 51 | 5 |

The results establish that, at the 2 mg level, compound I-2 is superior to the comparison compound with respect to processing time latitude (Trials 1 and 2 vs. Trials 8 and 9 or Trials 4, 6 and 7 vs. Trials 11, 13 and 14), processing temperature latitude (Trials 1, 3 and 6 vs. Trials 8, 10 and 13), tray vs. automatic processor (Trials 4 and 5 vs. Trials 11 and 12) and, lastly, general fog levels (Trials 6 and 7 vs. Trials 13 and 14).

observed by the comparison of Trials 1, 18 and 40 vs. 8, 28 and 53 or 4, 23, and 45 vs. 11, 33 and 58.

| Trial # | Part | Apparatus | (°C.) Temp | (Sec) Time | 100× Dmin | Toe | Mid | Shld | 10× Gamma | Pepper Level |
|---|---|---|---|---|---|---|---|---|---|---|
| 15 | B | Machine | 29 | 35 | 7 | 73 | 105 | 120 | 75 | 2 |
| 16 | " | " | 29 | 90 | 8 | 64 | 91 | 108 | 88 | 4 |
| 17 | " | " | 29 | 120 | 8 | 53 | 85 | 97 | 77 | 5 |
| 18 | " | " | 33 | 50 | 9 | 68 | 93 | 99 | 96 | 4 |
| 19 | " | " | 33 | 90 | 8 | 63 | 92 | 98 | 82 | 5 |
| 20 | " | " | 38 | 30 | 8 | 66 | 91 | 103 | 97 | 4 |
| 21 | " | Tray | 38 | 30 | 6 | 70 | 96 | 104 | 92 | 3 |
| 22 | " | Machine | 38 | 50 | 10 | 63 | 85 | 96 | 106 | 4 |
| 23 | " | " | 42 | 24 | 9 | 63 | 91 | 107 | 85 | 3 |
| 24 | " | " | 42 | 50 | 10 | 54 | 82 | 97 | 86 | 5 |
| 25 | E | Machine | 29 | 35 | 7 | 66 | 107 | 120 | 59 | 1 |
| 26 | " | " | 29 | 90 | 12 | 53 | 91 | 99 | 63 | 3 |
| 27 | " | " | 29 | 120 | 27 | 45 | 68 | 79 | 107 | 5+ |
| 28 | " | " | 33 | 50 | 10 | 53 | 87 | 100 | 71 | 3 |
| 29 | " | " | 33 | 90 | 20 | 45 | 79 | 91 | 71 | 4 |
| 30 | " | " | 38 | 30 | 8 | 49 | 90 | 105 | 59 | 3 |
| 31 | " | Tray | 38 | 30 | 6 | 53 | 79 | 89 | 92 | 2 |
| 23 | " | Machine | 38 | 50 | 21 | 39 | 80 | 94 | 58 | 5+ |
| 33 | " | " | 42 | 24 | 14 | 37 | 78 | 90 | 59 | 5+ |
| 34 | " | " | 42 | 50 | 75 | 11 | 61 | 66 | 48 | 5+ |

The results established that at the 4 mg level compound I-2 is again superior to the comparison compound with respect to processing time latitude (Trials 15, 16 and 17 vs. 25, 26 and 27 or Trials 20 and 22 vs. 30 and 32), processing temp. latitude (Trials 18, 22 and 24 vs. 28, 32 and 34), tray vs. automatic processor (Trials 20 and 21 vs. 30 and 31) and, lastly, general fog levels (Trials 17, 19 and 22 vs. 27, 29 and 32).

EXAMPLE 31

The emulsion described in example 28 was divided into parts G and H weighing 200 g. Each part was identically prepared for coating by the addition of sensitizing dye and coating aids such as those described in the previous examples. To the first part (Part G), 6 mg of compound I-2, 1-[4-(3-ethylthioureido) phenyl]-5-

| Trial # | Part | Apparatus | (°C.) Temp | (Sec) Time | 100× Dmin | Toe | Mid | Shld | 10× Gamma | Pepper Level |
|---|---|---|---|---|---|---|---|---|---|---|
| 35 | C | Machine | 29 | 40 | 5 | 71 | 103 | 126 | 75 | 2 |
| 36 | " | " | 29 | 65 | 7 | 66 | 99 | 121 | 74 | 5 |
| 37 | " | " | 29 | 120 | 16 | 53 | 82 | 99 | 83 | 5+ |
| 38 | " | " | 33 | 40 | 7 | 66 | 92 | 100 | 92 | 3 |
| 39 | " | Tray | 33 | 40 | 9 | 62 | 85 | 89 | 106 | 5+ |
| 40 | " | Machine | 33 | 50 | 9 | 61 | 88 | 103 | 91 | 5 |
| 41 | " | " | 33 | 90 | 11 | 55 | 84 | 109 | 83 | 5 |
| 42 | " | " | 38 | 17 | 6 | 70 | 101 | 122 | 78 | 2 |
| 43 | " | " | 38 | 40 | 9 | 61 | 92 | 112 | 78 | 5 |
| 44 | " | " | 38 | 50 | 10 | 62 | 87 | 91 | 94 | 5 |
| 45 | " | " | 42 | 24 | 9 | 62 | 89 | 98 | 89 | 3 |
| 46 | " | Tray | 42 | 24 | 12 | 62 | 84 | 88 | 111 | 5+ |
| 47 | " | Machine | 42 | 40 | 11 | 58 | 83 | 101 | 95 | 5 |
| 48 | F | Machine | 29 | 40 | 7 | 60 | 103 | 116 | 56 | 2 |
| 49 | " | " | 29 | 65 | 10 | 45 | 90 | 104 | 53 | 2 |
| 50 | " | " | 29 | 120 | 33 | 31 | 58 | 68 | 91 | 5+ |
| 51 | " | " | 33 | 40 | 7 | 47 | 93 | 115 | 53 | 3 |
| 52 | " | Tray | 33 | 40 | 6 | 47 | 67 | 77 | 118 | 5 |
| 53 | " | Machine | 33 | 50 | 16 | 33 | 76 | 96 | 56 | 5+ |
| 54 | " | " | 33 | 90 | 39 | 39 | 68 | 91 | 81 | 5+ |
| 55 | " | " | 38 | 17 | 7 | 61 | 105 | 120 | 54 | 1 |
| 56 | " | " | 38 | 40 | 20 | 37 | 75 | 88 | 63 | 5 |
| 57 | " | " | 38 | 50 | 40 | 29 | 64 | 101 | 68 | 5+ |
| 58 | " | " | 42 | 24 | 29 | 30 | 74 | 103 | 49 | 4 |
| 59 | " | Tray | 42 | 24 | 19 | 19 | 54 | 63 | 70 | 5+ |
| 60 | " | Machine | 42 | 40 | 89 | 12 | 71 | 100 | 41 | 5+ |

These results establish that at the 6 mg level compound I-2 is once again superior to the comparison compound with respect to processing time latitude (Trials 35 and 37 vs. 48 and 50 or 45 and 47 vs. 58 and 60), processing temperature latitude (Trials 35, 38, 43 and 47 vs. 48, 51, 56 and 60), tray vs. automatic processor (Trials 39 and 40 vs. 52 and 53 or 46 and 47 vs. 59 and 60), and lastly general fog levels (Trials 37, 41, 44 and 47 vs. 50, 54, 57 and 60).

Overall compound I-2 also exhibits less concentration dependency than the comparison compound. This is methyl semioxamazide, were added. To the remaining parts (Part H), 6 mg of the comparison compound 2-[4-(3-cyclohexylthioureido)phenyl]-1-formyl hydrazine, were added.

Finalled emulsions were coated at 4.2 g silver/m² on a polyester film support along with a protective overcoat layer containing a gelatin, dichlorohydroxytriazine, surfactants and matting agents. The emulsions were exposed using a tungsten light source for 4 seconds. The chemistry described previously was used for processing in either an automatic processing unit or in a tray.

5-nitroindazole to contrast and dot quality and U.S. Pat. No. 4,166,742—use of mercaptoazoles to reduce fog

| Trial # | Part | Apparatus | (°C.) Temp | (Sec) Time | 100× Dmin | Toe | Mid | Shld | 10× Gamma | Pepper Level |
|---|---|---|---|---|---|---|---|---|---|---|
| 61 | G | Machine | 29 | 40 | 5 | 82 | 126 | 136 | 55 | 1 |
| 62 | " | " | 29 | 65 | 5 | 78 | 114 | 133 | 67 | 1 |
| 63 | " | " | 29 | 120 | 5 | 73 | 101 | 113 | 84 | 1 |
| 64 | " | " | 33 | 40 | 6 | 77 | 118 | 129 | 58 | 1 |
| 65 | " | " | 33 | 50 | 6 | 74 | 110 | 133 | 66 | 1 |
| 66 | " | " | 33 | 65 | 5 | 75 | 107 | 137 | 75 | 1 |
| 67 | " | " | 33 | 90 | 6 | 68 | 96 | 120 | 85 | 2 |
| 68 | " | " | 38 | 17 | 6 | 77 | 114 | 134 | 65 | 1 |
| 69 | " | " | 38 | 24 | 6 | 75 | 113 | 131 | 64 | 1 |
| 70 | " | " | 38 | 30 | 6 | 72 | 101 | 138 | 81 | 1 |
| 71 | " | Tray | 38 | 30 | 5 | 74 | 96 | 105 | 108 | 1 |
| 72 | " | Machine | 38 | 40 | 6 | 71 | 105 | 119 | 70 | 1 |
| 73 | " | Machine | 38 | 50 | 7 | 67 | 92 | 101 | 96 | 2 |
| 74 | " | " | 42 | 17 | 7 | 71 | 104 | 133 | 72 | 1 |
| 75 | " | " | 42 | 24 | 7 | 66 | 99 | 116 | 73 | 1 |
| 76 | " | Tray | 42 | 24 | 5 | 71 | 96 | 123 | 95 | 1 |
| 77 | " | Machine | 42 | 30 | 8 | 69 | 97 | 106 | 86 | 1 |
| 78 | " | " | 42 | 40 | 8 | 62 | 95 | 104 | 73 | 1 |
| 79 | H | Machine | 29 | 40 | 5 | 80 | 129 | 141 | 49 | 1 |
| 80 | " | " | 29 | 65 | 5 | 75 | 124 | 140 | 49 | 1 |
| 81 | " | " | 29 | 120 | 7 | 65 | 97 | 104 | 75 | 1 |
| 82 | " | " | 33 | 40 | 5 | 72 | 123 | 139 | 47 | 1 |
| 83 | " | " | 33 | 50 | 7 | 64 | 96 | 112 | 75 | 1 |
| 84 | " | " | 33 | 65 | 6 | 65 | 97 | 118 | 75 | 1 |
| 85 | " | " | 33 | 90 | 9 | 60 | 92 | 102 | 74 | 1 |
| 86 | " | " | 38 | 17 | 5 | 71 | 126 | 135 | 44 | 1 |
| 87 | " | " | 38 | 24 | 7 | 69 | 105 | 125 | 68 | 1 |
| 88 | " | " | 38 | 30 | 7 | 64 | 107 | 131 | 56 | 2 |
| 89 | " | Tray | 38 | 30 | 5 | 47 | 71 | 75 | 101 | 5 |
| 90 | " | Machine | 38 | 40 | 7 | 59 | 87 | 96 | 85 | 3 |
| 91 | " | " | 38 | 50 | 8 | 53 | 85 | 101 | 76 | 5 |
| 92 | " | " | 42 | 17 | 7 | 63 | 106 | 131 | 56 | 2 |
| 93 | " | " | 42 | 24 | 8 | 50 | 87 | 103 | 66 | 3 |
| 94 | " | Tray | 42 | 24 | 6 | 32 | 64 | 74 | 76 | 4 |
| 95 | " | Machine | 42 | 30 | 10 | 29 | 81 | 93 | 46 | 4 |
| 96 | " | " | 42 | 40 | 17 | 11 | 59 | 84 | 50 | 5+ |

The results establish that, at the 6 mg level, compound I-2 is superior to the comparison compound with respect to processing time latitude (Trials 61–63 vs. 79–81, 64–67 vs. 82–85, 68–73 vs. 86–91 or 74–78 vs. 92–96), processing temperature latitude (61, 64, 72 and 78 vs. 79, 82 90 and 96), tray vs. automatic processor (Trials 70, 71 vs. 88, 89 or 75, 76 vs. 93, 94) and lastly, general fog levels (Trials 77, 78 vs. 95, 96).

The overall conclusion that can be drawn from these data is that the semioxamazide derivative, compound I-2, performs in a superior fashion to that of its formyl hydrazide analog. This can be observed in either a high-chloride, "lith type" emulsion or a straight bromide emulsion. Improvements can be found in pepper levels, processing latitude, fogging tendency, concentration independency and lastly tray-automatic processor variations. Although the prior art teaches the use of various additives in systems using formyl hydrazines to improve upon several parameters (e.g., U.S. Pat. No. 4,416,969—use of two hydrazides to improve processing temperature latitude; U.S. Pat. No. 4,311,781—use of tetrazaindolizines to reduce fog levels; U.S. Pat. No. 4,237,214—use of azolium salts to reduce fog levels; U.S. Pat. No. 4,221,857—use of polyethylene oxides and 5-nitroindazole to contrast and dot quality and U.S. Pat. No. 4,166,742—use of mercaptoazoles to reduce fog levels) the instant invention does not require the use of these agents.

EXAMPLE 32

The emulsion described in Example 28 was divided into parts I and J each weighing 200 g. Both parts were identically prepared for coating by the addition of a sensitizing dye, coating aids and compound I-2. 13.3 ml of a 4.3M sodium formaldehyde bisulfite solution were also added to part J.

The finalled emulsions were coated at 3.9 g silver/$m^2$ on a polyester film support along with a protective overcoat layer containing gelatin, dichlorohydroxytriazine, surfactants and matting agents. The emulsions were exposed using a tungsten light source for 4 seconds. The chemistry described above was used for processing in either an automatic processing unit or in a tray.

| Trial # | Part | Apparatus | Temp | Time | 100× Dmin | Toe | Mid | Shld | 10× Gamma | Pepper Level | Dot Quality |
|---|---|---|---|---|---|---|---|---|---|---|---|
| 97 | I | Machine | 38 | 38 | 9 | 61 | 92 | 112 | 78 | 4 | 2 |
| 98 | " | Tray | 39 | 35 | 5 | 62 | 94 | 115 | 79 | 5 | 2 |
| 99 | J | Machine | 38 | 38 | 8 | 68 | 99 | 119 | 78 | 3 | 2 |
| 100 | " | Tray | 38 | 35 | 4 | 70 | 97 | 122 | 80 | 2 | 1 |

These results demonstrate that sodium formaldehyde bisulfite can be used to reduce the pepper level especially when tray processing is employed.

The invention has been described in detail with particular reference to preferred embodiments thereof, but

What is claimed is:

1. A compound of the formula

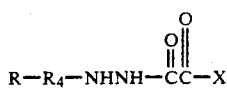

wherein: R is

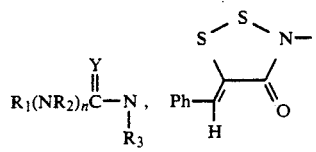

where
Ph is phenyl, or

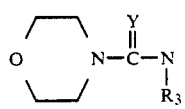

X is —NR$_5$R$_6$ or —OR$_7$;
R$_1$ and R$_2$ are independently selected from the group consisting of hydrogen, methyl, ethyl, cyclohexyl,

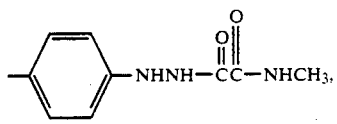

butyl, or heptyl;
R$_4$ is o-phenylene or p-phenylene and R$_4$ can be alkyl- halo- or alkoxy- substituted;
R$_3$ is hydrogen;
R$_5$, R$_6$, and R$_7$ are independently selected from the group consisting of hydrogen, methyl, ethyl, tert-butyl, isobutyl, butyl, alkoxy, acyl, acylamino, aryl, amino, cyclohexyl, aminoalkyl and substituted or unsubstituted phenylamino;
Y is selected from the group consisting of sulfur and oxygen atom; and n is zero or 1; provided n=1 when Y is sulfur.

2. A compound of the formula

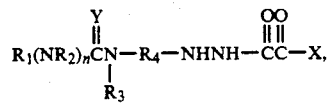

wherein X=NR$_5$R$_6$, Y=S, and N=1;

R$_1$ and R$_2$ are independently selected from the group consisting of hydrogen, methyl, ethyl, cyclohexyl, and

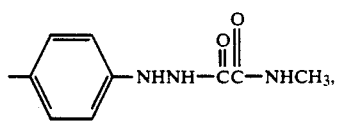

or R$_1$ and R$_2$ are linked together with the adjacent amino nitrogen to form a morpholino- group, or R$_1$ is linked with R$_3$ to form a heterocyclic group having 3–10 carbon atoms; R$_3$ when not linked with R$_1$ is hydrogen or benzyl and
R$_4$ is selected from the group of para-phenylene and methyl-substituted para-phenylene.

3. A compound according to claim 1, wherein Y=S.
4. A compound according to claim 1, wherein Y=O.
5. A compound according to claim 1, wherein X=NR$_5$R$_6$.
6. A compound according to claim 1, wherein X=OR$_7$.
7. A compound according to claim 1 wherein:
X=OR$_7$, Y=S;
R$_1$ and R$_2$ are selected from the group consisting of hydrogen and cyclohexyl;
R$_3$ is hydrogen;
R$_4$ is para-phenylene; and
R$_7$ is ethyl.
8. A compound according to claim 1 wherein:
X=NR$_5$R$_6$, Y=O;
R$_1$ and R$_2$ are selected from the group consisting of hydrogen, butyl, and heptyl;
R$_4$ is para-phenylene; and
R$_5$ and R$_6$ are selected from the group consisting of hydrogen and methyl.
9. A compound according to claim 1 of the formula:

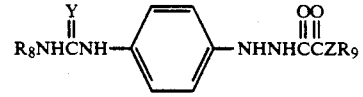

wherein Y=O or S; Z=O or NH; R$_8$ is selected from the group constituting R$_2$ except R$_8$ is not hydrogen; and R$_9$ is selected from the group constituting R$_5$.

10. A compound according to claim 9 wherein R$_8$ is ethyl and R$_9$ is amino; Y=S and Z=NH.
11. A compound according to claim 9 wherein R$_8$ is cyclohexyl and R$_9$ is acetylamino.
12. A compound according to claim 9 wherein R$_8$ is cyclohexyl and R$_9$ is amino.
13. A compound according to claim 9 wherein R$_1$ is hydrogen, R$_2$ is butyl and R$_5$, R$_6$ are hydrogen.
14. A compound according to claim 9 wherein R$_1$ is hydrogen, R$_2$ is butyl, R$_5$ is hydrogen and R$_6$ is methyl.

* * * * *